(12) United States Patent
Shen

(10) Patent No.: US 7,865,371 B2
(45) Date of Patent: Jan. 4, 2011

(54) MANAGEMENT OF INFORMATION FLOW AND WORKFLOW IN MEDICAL IMAGING SERVICES

(76) Inventor: Michael Y. Shen, 520 Collings Ave., B-919, Collingswood, NJ (US) 08107

( * ) Notice: Subject to any disclaimer, the term of this patent is extended or adjusted under 35 U.S.C. 154(b) by 2018 days.

(21) Appl. No.: 10/435,588

(22) Filed: May 12, 2003

(65) Prior Publication Data

US 2003/0212580 A1 Nov. 13, 2003

Related U.S. Application Data

(60) Provisional application No. 60/378,946, filed on May 10, 2002.

(51) Int. Cl.
*G06Q 50/00* (2006.01)
(52) U.S. Cl. .......................................................... 705/2
(58) Field of Classification Search ....................... 705/2
See application file for complete search history.

(56) References Cited

U.S. PATENT DOCUMENTS

| | | |
|---|---|---|
| 4,731,725 A | 3/1988 | Suto et al. |
| 5,319,543 A | 6/1994 | Wilhelm |
| 5,335,292 A | 8/1994 | Lovelady et al. |
| 5,660,176 A | 8/1997 | Iliff |
| 5,711,297 A | 1/1998 | Iliff |
| 5,724,968 A | 3/1998 | Iliff |
| 5,746,204 A | 5/1998 | Schauss |
| 5,868,669 A | 2/1999 | Iliff |
| 5,910,107 A | 6/1999 | Iliff |
| 5,911,132 A | 6/1999 | Sloane |
| 5,953,704 A * | 9/1999 | McIlroy et al. .................. 705/2 |
| 5,974,389 A | 10/1999 | Clark et al. |
| 6,018,713 A | 1/2000 | Coli et al. |
| 6,022,315 A | 2/2000 | Iliff |
| 6,029,138 A | 2/2000 | Khorasani et al. |
| 6,049,794 A | 4/2000 | Jacobs et al. |
| 6,157,929 A | 12/2000 | Zamiska et al. |
| 6,206,829 B1 | 3/2001 | Iliff |
| 6,223,164 B1 | 4/2001 | Seare et al. |
| 6,226,620 B1 | 5/2001 | Oon |
| 6,234,964 B1 | 5/2001 | Iliff |
| 6,246,975 B1 | 6/2001 | Rivonelli et al. |
| 6,272,470 B1 | 8/2001 | Teshima |
| 6,283,761 B1 | 9/2001 | Joao |
| 6,324,516 B1 * | 11/2001 | Shults et al. .................... 705/2 |
| 6,349,330 B1 | 2/2002 | Bernadett et al. |
| 6,353,817 B1 | 3/2002 | Jacobs et al. |
| 6,356,873 B1 | 3/2002 | Teagarden et al. |

(Continued)

OTHER PUBLICATIONS

Barry R Furrow. American Journal of Law and Medicine. Boston: 1999. vol. 25, Iss. 2/3; p. 403, 19 pgs.*

*Primary Examiner*—Robert W Morgan
*Assistant Examiner*—Robert Sorey
(74) *Attorney, Agent, or Firm*—Cahn & Samuels, LLP

(57) ABSTRACT

Managing information flow and workflow in medical imaging services includes mapping activities in medical imaging services to a set of discrete steps in a model medical imaging process. Data concerning the medical imaging services is collected and tracked using an electronic data store and a communications network. Collected data is correlated to at least one of the discrete steps in the model medical imaging process and process metrics for performance are calculated based upon the correlated data.

44 Claims, 28 Drawing Sheets

U.S. PATENT DOCUMENTS

| | | |
|---|---|---|
| 6,381,576 B1 | 4/2002 | Gilbert |
| 6,424,996 B1 | 7/2002 | Killcommons et al. |
| 6,430,428 B1 | 8/2002 | Lindstedt |
| 6,463,417 B1 | 10/2002 | Schoenberg |
| 6,468,210 B1 | 10/2002 | Iliff |
| 6,475,143 B2 | 11/2002 | Iliff |
| 6,482,156 B2 | 11/2002 | Iliff |
| 6,524,241 B2 | 2/2003 | Iliff |
| 6,527,713 B2 | 3/2003 | Iliff |
| 6,904,161 B1 * | 6/2005 | Becker et al. ............... 382/128 |
| 7,383,196 B1 * | 6/2008 | Tang et al. ..................... 705/3 |
| 2001/0029509 A1 * | 10/2001 | Smith et al. ............... 707/104.1 |
| 2001/0053984 A1 | 12/2001 | Joyce et al. |
| 2002/0016821 A1 | 2/2002 | Son et al. |
| 2002/0019751 A1 | 2/2002 | Rothschild et al. |
| 2002/0052540 A1 | 5/2002 | Iliff |
| 2002/0062068 A1 | 5/2002 | Gritzbach et al. |
| 2002/0072933 A1 | 6/2002 | Vonk et al. |
| 2002/0099686 A1 * | 7/2002 | Schwartz et al. ............... 707/1 |
| 2002/0184325 A1 | 12/2002 | Killcommons et al. |
| 2002/0188597 A1 * | 12/2002 | Kern et al. ..................... 707/1 |
| 2002/0194029 A1 | 12/2002 | Guan et al. |
| 2003/0033268 A1 | 2/2003 | Muthya |
| 2003/0045782 A1 | 3/2003 | Iliff |
| 2003/0050821 A1 * | 3/2003 | Brandt et al. .................. 705/9 |
| 2003/0093294 A1 * | 5/2003 | Passantino .................... 705/2 |
| 2003/0110060 A1 * | 6/2003 | Clementi ....................... 705/2 |
| 2004/0015372 A1 * | 1/2004 | Bergman et al. ............... 705/3 |

* cited by examiner

900

Infoflow & Workflow Management

*Nuclear Cardiology*     Physician Information System

Global Risk Scores

- Patient List
- Test Ordering
  - Risk Scores
  - Indications
  - Test Ordering
  - Summary
- View Test Order
- Email Exit

Patient Information

*Patient Social Security Number: 78

*First Name: Bill     Middle Name:     *Last Name: Smith

*Sex: M    *Date of Birth: 12/3/1941    Referral MD: Mike Smith

- Medical History
  - Risk Factors
    - Family history for coronary heart disease: Yes
    - Years of Smoking: 12

|  | Workflow | Information Flow | |
|---|---|---|---|
|  | Statistics | Efficiency | Accuracy |
| 1. | Validation (311) | Standardization (313) | |
| Standard resources | Practice guidelines or standards | Time from the date of publications to patient care | Level of standard (national, local, etc) |
| 2. | Tests & Indications (312) | Dissemination (314) | |
| Risk Assessment | # pts with risk(s) for assessment / Total pts with risk(s) | Time (Mon,Yr) to get __% (default 50%) pts with risk(s) assessed | # pts truly with the risk(s) / total pts with risk(s) |
| Test applications | # pts thought indicated and referred / total pts indicated | Time (Mon,Yr) to get __% (default 50%) pts indicated to referred | # pts truly indicated / total pts indicated |
| 3. | Test Ordering (321) | Access (323) | |
| Scheduling | # indicated pts scheduled / Total pts referred | Time (Days, Mon) to get indicated pts scheduled | # pts scheduled / total pts indicated |
| Priority | # pts prioritized / total pts need priority | Time (Days, Mon) to pts with priority for scheduling | # pts prioritized / total pts indicated |
| Test selection | # pts selected for the test / total pts referred | Time (Days, Mon) to select pts for given testing | # pts test selected right / total pts selected |
| Protocol selection | # pts protocol selected / total pts referred | Time (Days, Mon) to select pts for given protocol | # pts protocol selected right / total pts selected |
| 4. | Reporting (322) | Distribution (324) | |
| Results delivery | # pts results delivered / total pts with results | Time (Hrs, days) to sent results to patients/referrals | # pts received the results / total pts with the results |
| Results understanding | # pts results understood / total pts with results | Time (Hrs, days) to understand the results | # pts' results understood / total pts with the results |
| Risk classification | # pts' risk understood / total pts with results | Time (Hrs, days) to sent results to patients/referrals | # pts classified right / total pts with the results |
| 5. | Follow-up (331) | Adoption (332) | |
| Management | # pts changed management / total pts with results | Time (days, Mon, Yrs) to change the pts management | # pts actually changed management / total pts need to change |
| Consult | # pts to see consults / total pts need consults | Time (Hrs, days) for the pts to see consults | # pts actually need consults / # pts to see consults |

| Patient selection | Patients with diabetes AND hypertension AND hypercholesterolemia AND asymptomatic |
|---|---|
| Time periods | From: 1/1/2000  To: 1/1/2002 |
| Total patients: | 2,000 |

| | Workflow | | Information Flow | |
|---|---|---|---|---|
| | Statistics | | Efficiency | Accuracy |
| Validation (311) | | | Standardization (313) | |
| Resource | • ADA: Feb 10, 1998 | | 2-4 years | Expert consensus |
| Tests & Indications (312) | | | Dissemination (314) | |
| *Risk Assessment* | 500/2000 (25%) | | 3.2 years | |
| *Test applications* | 200/1800 (11%) | | 2.8 years | 190/200 (95%) |
| Test Ordering (321) | | | Access (323) | |
| *Priority* | 40/200 (20%) | | 3 Days | 60/200 (30%) |
| *Test selection* | Referred | Selected | 6 days | Inaccurate rate: 75/200 (37.5%) |
| ETT | 50 (25%) | 5 (2.5%) | | |
| Stress Echo | 75 (37.5%) | 45 (22.5%) | | |
| Stress MPI | 75 (37.5%) | 150 (75%) | | |
| *Agent selection* | | | 6 days to select given testing | Inaccurate rate: 100//200 (50%) |
| Tl-201 | 100 (50%) | 5 (2.5%) | | |
| MIBI | 50 (25%) | 150 (75%) | | |
| Tetro | 50 (25%) | 45 (22.5%) | | |
| *Stress selection* | | | 6 days to select given testing | Inaccurate rate: 60/200 (30%) |
| Exercise | 150 (75%) | 100 (50%) | | |
| Adenosine | 10 (5%) | 70 (35%) | | |
| Dipyridamole | 30 (15%) | 25 (12.5%) | | |
| Dobutamine | 10 (5%) | 5 (2.5%) | | |
| Reporting (322) | | | Distribution (324) | |
| *Results & delivery* | 160 normal (80%) 40 abnormal (20%) • 10 with mild risk | | # 40 (20%) same day # 60 (30 %) 2 days # 100 (50%) >2 days # 20 (50%) ABNL right away | Outcomes Analysis |
| *Results Understanding* | • 25 with moderate risk • 5 with high risk | | | |
| *Risk classification* | | | | |
| Follow-up (331) | | | Adoption (332) | |
| *Post-Test Risk Assessment* | • Low: 170 (85%) • Moderate: 25 (12.5%) • High: 5 (2.5%) | | 3.2 years to be tested | Outcomes Analysis |
| *Management* | Pre-test | Post-test | 3.2 years to change management | |
| *Med Tx/Observe* | 50 (25%) | 150 (75%) | | |
| *Other noninvas..* | 0 (0%) | 20 (10%) | | |
| *Invasive test* | 0 (0%) | 30 (15%) | | |
| *Consult* | 20/200 (10%) referred 20/40 (50%) abnormal | | 3.2 years to see consults | 20/40 50 (%) |

Diagnostic outcomes

| | Invasive Testing Rate (Example: Cath) | Interventional Rate (Example: PTCA) | Surgery Rate (Example: Bypass) |
|---|---|---|---|
| Utilization | # cathed pts with nl or abnl scan / total of pts with nl or abnl scans | # PTCA pts with abnl scan / total of pts with abnl scans | # Bypass pts with abnl scan / total of pts with abnl scans |
| Accuracy | Diagnosis (Patients)<br>Specific patient population:<br>Sensitivity:<br>Specificity:<br><br>Individual patient:<br>Positive Predictive Value:<br>Negative Predictive Value: | Anatomy (Coronary Territories)<br>• Single vessel disease:<br>Left anterior descending<br>Left Circumflex<br>Right coronary artery<br>• Multi-vessel disease:<br>2 vessel disease<br>3 vessel disease | Comparison with Other Imaging Modalities<br>VS. Stress Echo:<br>Sensitivity:<br>Specificity:<br><br>VS. Stress MRI:<br>Sensitivity:<br>Specificity: |
| Clinical Correlation | Agreement<br># agreed results / total # results of the test | Uncertainty<br># uncertain results / total # results of the test | Disagreement<br># disagreed results / total # results of the test |

Clinical Outcomes

2500

| | Hospitalization | Complications | Myocardial Infarction | Death |
|---|---|---|---|---|
| *Event Rates* | # pts hospitalized / total # with result | # pts with complications / total # with result | # pts with MIs / total # with results | # death pts / total # with results |
| | Dates | Patient Response | MD Response | Agreement |
| *Symptoms* Asymptomatic | | # pts response as being asymptomatic | # MDs response as being asymptomatic | Pts vs. MDs |
| New symptoms | | # pts response as being symptomatic | # MDs response as being symptomatic | Pts vs. MDs |
| | Dates | Results 1 | Results 2 | Difference Results 2 – Results 1 |
| *Testing Indexes* | Initial Test Date | | | |
| | Follow-up Test Date | | | |

Fig. 25

Service Outcomes

| Procedures | Total Volume | | Benchmark | Optimal/Potential |
|---|---|---|---|---|
| *GSPECT/year* | A | | B | C |
| *Difference/year* | | | A-B | A-C |
| *Est. Revenue/year* | | | | |
| Referrals | MD Vol. | Pt. Vol. | Referral Resources | Potential |
| *Physicians* | Specialty A: | # | # towns (# zip codes) | # towns (# zip codes) |
| | Specialty B: | # | # towns (# zip codes) | # towns (# zip codes) |
| | ... | ... | ... | ... |
| | Specialty Z: | # | # towns (# zip codes) | # towns (# zip codes) |
| *Special Patient population* | Total Volume | | Benchmark | Optimal/Potential |
| | | | % population | |
| | | | % population | |
| Satisfaction | | | Patients | Referral MDs | Differences |
| Scheduling | | | % | % | Patients – Referral MDs |
| Preparation | | | % | % | Patients – Referral MDs |
| Report | | | % | % | Patients – Referral MDs |
| Clerical | | | % | % | Patients – Referral MDs |

Financial Outcomes

| | | | |
|---|---|---|---|
| *Reimbursed* | Volume<br>Total:<br># (total %) | Billing cycle<br>Average: weeks/months<br>  o majority%: weeks<br>  o minority%: weeks | Benchmark<br>Average: weeks/months<br>  o majority%: weeks<br>  o minority%: weeks |
| *Inadequate reimbursement* | Volume<br># (total %) | Reasons<br># (total%) Not covered in _____ insurance companies. | Follow-up<br># (total%) with uncorrected coding in billing<br>- # (total%) $2^{nd}$, $3^{rd}$ try |
| *Cost*<br>- Personnel:<br>- Agents:<br>- Equipments:<br>- Real Estate<br>- Ect | Number<br>#<br>#<br>#<br># | Costs<br>$<br>$<br>$<br>$ | Total<br># × $<br># × $<br># × $<br># × $ |
| *Cost-Benefits* | Revenue/Year<br>$ | Benchmark<br>$ | Potential<br>$ |

Fig. 27

Statistical & Factor Analysis

2800

| Factors | | Prediction Power $\chi^2$ | Diagnostic | Outcomes | | | Patient Volumes |
|---|---|---|---|---|---|---|---|
| Index | Time | | | Hospitalized | MI | Death | |
| Hx of MI | >1 yr | 40 (p<0.001) | PPV: 85% NPV: 80% | 5 | 3 | 1 | 100 (6.7%) |
| Hba1c>8 | >5 yrs | 35 (p<0.001) | PPV: 60% NPV: 85% | 3 | 1 | 0 | 200 (13%) |
| SBP>160 | >10 yrs | 30 (p<0.01) | PPV: 50% NPV: 75% | 2 | 0 | 0 | 300 (20%) |
| LDL>160 | >8 yrs | 28 (p<0.01) | PPV: 45% NPV: 60% | 0 | 0 | 0 | 300 (20%) |
| Age | >50 yrs | 25 (p<0.05) | PPV: 25% NPV: 50% | 0 | 0 | 0 | 600 (40%) |
| Summary | | | PPV: 82% NPV: 92% | 10 | 30 | 5 | 1500 |

Fig. 28

MANAGEMENT OF INFORMATION FLOW AND WORKFLOW IN MEDICAL IMAGING SERVICES

CROSS REFERENCE TO RELATED APPLICATIONS

This application claims the benefit of U.S. Provisional Application No. 60/378,946, filed May 10, 2002, and titled "Management of Information Flow and Workflow in Medical Imaging Services," which is incorporated by reference in its entirety.

TECHNICAL FIELD

This document relates to the management of information flow and workflow in medical imaging services.

BACKGROUND

In general, diagnostic imaging services have been playing a critical role in detecting diseases as the first step in healthcare. The cost of imaging services is an estimated one-third of healthcare costs per year. Diagnostic imaging service in the healthcare delivery is a complex workflow process with many personnel and services involved. This process is an information-based transaction. Improving the workflow and information transformation process is a key to improving the quality and cost savings of healthcare.

SUMMARY

In one general aspect, managing information flow and workflow in medical imaging services includes mapping activities in medical imaging services to a set of discrete steps in a model medical imaging process. Data concerning the medical imaging services is collected and tracked using an electronic data store and a communications network. Collected data is correlated to at least one of the discrete steps in the model medical imaging process and process metrics for performance are calculated based upon the correlated data.

Implementations may include one or more of the following features. For example, workflow activities and/or information flow activities in the medical imaging services may be mapped to the set of discrete steps in the model medical imaging process. Data from the workflow activities and/or the information flow activities in the medical imaging services may be collected and tracked. In one implementation, data from the workflow activities and/or the information flow activities of all parties involved in the medical imaging services may be collected and tracked using a communication network.

Pre-testing activities in the medical imaging services may be mapped to the set of discrete steps in the model medical imaging process. The pre-testing activities may include at least one of validation, tests and indications, standardization, and dissemination. Testing activities in the medical imaging services may be mapped to the set of discrete steps in the model medical imaging process. The testing activities may include at least one of test ordering, reporting, access, and distribution. Post-testing activities in the medical imaging services may be mapped to the set of discrete steps in the model medical imaging process. The post-testing activities may include at least one of follow-ups, adoption, and outcomes.

Process metrics may include flow metrics that correspond to one or more the discrete steps in the model medical imaging process based on the correlated data. One or more limiting steps in the model medical imaging process may be identified using the flow metrics. The flow metrics may be presented to a user in an order following the discrete steps in the model medical imaging process to enable the user to identify one or more limiting steps in the model medical imaging process.

Flow metrics may include workflow statistics that are presented to a user in an order following the discrete steps in the model medical imaging process, where the workflow statistics correspond at least to steps of pre-testing, testing, and post-testing. Flow metrics may include information flow statistics that are presented to a user in an order following the discrete steps in the model medical imaging process, where the information flow statistics provide a measure of efficiency and accuracy related to the discrete steps in the model medical imaging process.

The process metrics also may include outcome metrics that correspond to a combination of the discrete steps in model medical imaging process based on the correlated data. The outcome metrics may include diagnostic metrics. The diagnostic metrics may include utilization metrics to track an impact of using a screening test in the medical imaging services on at least one of further other non-invasive testing, invasive testing, interventional therapy, and surgery. The diagnostic metrics may include accuracy metrics to measure diagnostic test accuracy in terms of patients and specific anatomy in comparison to other invasive or non-invasive tests. The diagnostic metrics may include clinical correlation metrics to track feedback from referral physicians to results of tests on patients of the referral physician.

The outcome metrics may include clinical outcome metrics. The clinical outcome metrics may include event rate metrics to track feedback related to clinical complications and events using a communication network. A clinical outcome metric may include symptom metrics to track changes in a patient's symptoms. The clinical outcome metrics may include testing index metrics to measure physiological functions of a patient as a result of patient treatment.

The outcome metrics may include service outcome metrics. The service outcome metrics may include procedure outcome metrics to track multiple procedure utilizations over a period of time at a particular medical imaging center as compared with benchmark targets and/or organizational goals. The service outcome metrics may include referral outcome metrics to track referral physician specialties and practice locations as compared with benchmark targets and/or organizational goals.

The outcome metrics may include financial outcome metrics. The financial outcome metrics may include reimbursement metrics to measure a billing performance based on a reimbursement rate and speed compared to a benchmark target and/or organizational goals. The financial outcome metrics may include inadequate reimbursement metrics to measure a billing performance based on a total number of non-reimbursed patients and a reason for non-reimbursements.

Arrays of data and metrics may be generated to enable exporting the data and metrics to statistical analysis computer software for further analysis. A tool may be provided to input and modify medical standards for comparison to metrics from at least one of the discrete steps or measures in the model medical imaging process. The input medical standards may be correlated to modifiable reimbursement codes and recommendation levels.

Analysis metrics may be generated based on an integration of different users of the communications network, different test and results, and the process metrics to enable a comprehensive analysis of different aspects of the medical imaging services. The analysis metrics may include utilization metrics for measuring medical imaging tests actually performed compared with recommended medical imaging tests based on medical guideline recommendations to identify under-utilization and over-utilization of particular medical imaging tests.

The analysis metrics may include referral analysis metrics for identifying referral patterns of referral physicians in relation to patients, tests, and process and outcome metrics. The analysis metrics may include service and marketing metrics for identifying potential service areas compared with modifiable benchmarks or organizational goals.

The analysis metrics may include clinical risk assessment metrics for use in at least one of pre-testing risk stratification and post-testing risk stratification.

The analysis metrics may include clinical risk assessment metrics to use an established or published model to assess risks in given patients and a need for further diagnostic imaging tests. The analysis metrics may include clinical risk assessment metrics to use an established or published model to assess risks in given patients and compare to post imaging risk classification to assess the established or published model. The analysis metrics include clinical risk assessment metrics to use an established or published model to assess risks in given patients and compare to patient clinical outcomes to assess the established or published model.

The analysis metrics may include behavior analysis metrics to evaluate behavior patterns of at least one of referral physicians, medical imaging centers, and patients compared to standards and outcomes in the model medical imaging process over a period of time.

The analysis metrics may include organizational process analysis metrics to identify one or more steps in the entire process for improvement in organizational performance for different outcomes.

The analysis metrics may include organizational process analysis metrics to examine one or more steps in the entire process to reengineer one or more new steps or process for improvement in organizational performance for different outcomes. The analysis metrics may include practice process analysis metrics to analyze longitudinal practice from clinical question, to testing, diagnosis and risk stratification, follow-up/clinical management and clinical outcomes. The analysis metrics may include test selection analysis metrics to compare different tests. The analysis metrics may include cost effectiveness analysis metrics to compare different tests in a cost and benefit analysis.

The analysis metrics may include local practice analysis metrics for use in developing of local database system to measure and track the degree of standard implementation, the difference of patients and practice between national and local, and refinement of local standardization.

The local practice analysis metrics may include metrics for use in measuring and tracking the degree of implementing national standards and guidelines for quality control, improve insurance reimbursement and monitoring legal protection. The local practice analysis metrics may include metrics to define the difference of patients and practice between national and local levels for patient population characteristics in disease development, progress and response to treatment as well as patient reception to new technologies and treatment. The local practice analysis metrics may include metrics to define the difference of practice between national and local level to identify the realistic level of local expertise to the national standards in local practice capabilities and technology requirement. The local practice analysis metrics may include metrics to define the difference of practice between national and local level to identify local practice variation from national criteria and standards in diagnosis and diagnostic accuracies to redefine local standards in local practice or recommend new local practice criteria.

The analysis metrics may include outcome estimation and modification in using indexes of an imaging test to estimate local patient outcomes, track real outcomes and refine indexes for patient outcome estimation. The analysis metrics may include outcome estimation of local patient clinical outcomes based on published landmark studies in certain local patient populations to see the difference in estimation. The analysis metrics may include outcome estimation refinements in using a database to track and follow-up with patients over time to observe the real outcomes. The analysis metrics may include outcome estimation to further refine indexes for patient outcome estimation with respect to patient characteristics or technology.

Functions or performances of the medical imaging services may be calculated using metrics based on the correlated data. Collected data and metrics may be extrapolated for further analysis.

These general and specific aspects may be implemented using a system, a method, or a computer program, or any combination of systems, methods, and computer programs.

Other features will be apparent from the description and drawings, and from the claims.

DESCRIPTION OF DRAWINGS

FIGS. 4-21 are exemplary screen shots of a graphical user interface.

FIG. 22 is an exemplary table illustrating flow metrics calculated as part of the exemplary process of FIG. 3.

FIG. 23 is an exemplary table illustrating an example of a filled-out table from FIG. 22.

FIGS. 24-28 are exemplary tables illustrating different outcome metrics resulting from the process of FIG. 3.

Like reference symbols in the various drawings indicate like elements.

DETAILED DESCRIPTION

1. Communication Infrastructure

Personnel, Locations, Computers and Network Systems

For brevity, several elements in the figures described herein are represented as monolithic entities. However, as would be understood by one skilled in the art, these elements each may include numerous interconnected computers and components designed to perform a set of specified operations and/or may be dedicated to a particular location and/or geographical region.

Figure 1:
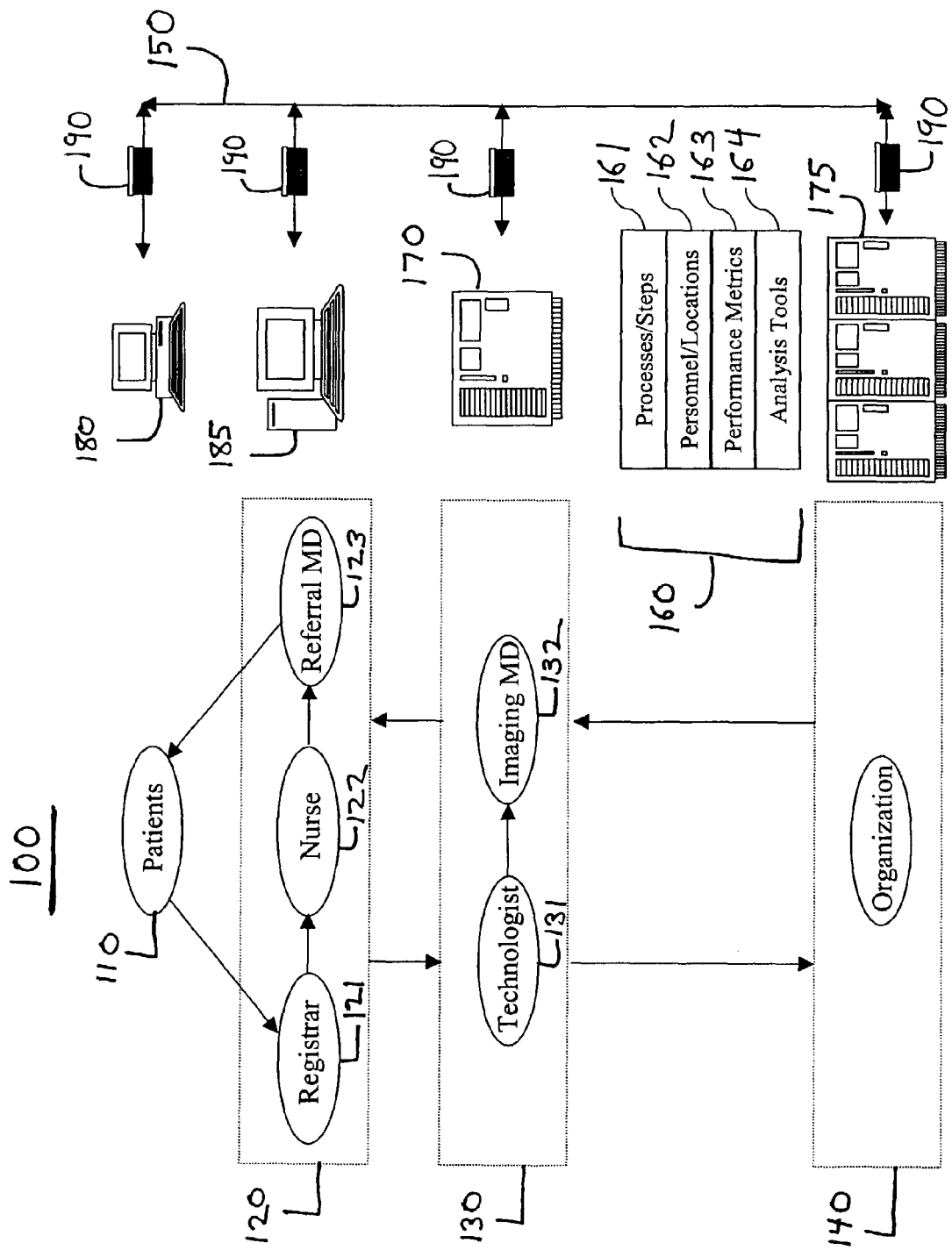
FIG. 1 is a block diagram of a communications system for managing information flow and workflow in medical imaging services.

Referring to FIG. 1, a communications system 100 for managing information flow and workflow in medical imaging services enables communications between multiple, different people or groups of people at different locations, such as patients 110, medical practice personnel 120 (e.g., registrars 121, nurses 122, and referring physicians 123), medical imaging personnel 130 (e.g., technologists 131 and imaging physicians 132, including cardiologists, radiologists and any specialty physicians interpreting imaging tests), and organizations 140 (e.g., government entities, hospital systems, insurance related entities, pharmaceutical related entities, medical equipment entities and numerous other healthcare related entities). The communications are provided over a communications network 150. More specifically, for example, the communications system 100 enables the different people or groups of people at different locations to access and exchange communications and data over the communications network 150 with one or more electronic data stores 160 and servers 170 and 175.

The patients 110, medical personnel 120, medical imaging personnel 130, and organizations 140 typically access the communications network 150 through a computing device, such as one of computing devices 180 and 185. Computing devices 180 and 185 may include, for example, general-purpose computers (e.g., personal computers), special-purpose computers (e.g., devices specifically programmed to communicate with each other and/or other components on the communications network 150), or a combination of one or more general-purpose computers and one or more special-purpose computers. The computing devices 180 and 185 may be arranged to operate within or in concert with one or more other systems, such as, for example, one or more local area networks (LANs) and/or one or more wide area networks (WANs). Other examples of computing devices 180 and 185 may include a workstation, a terminal, a personal digital assistant (PDA), other physical or virtual equipment, or some combination thereof capable of responding to and executing instructions. Computing devices 180 and 185 may be capable of conducting peer-to-peer communications.

Figure 2:
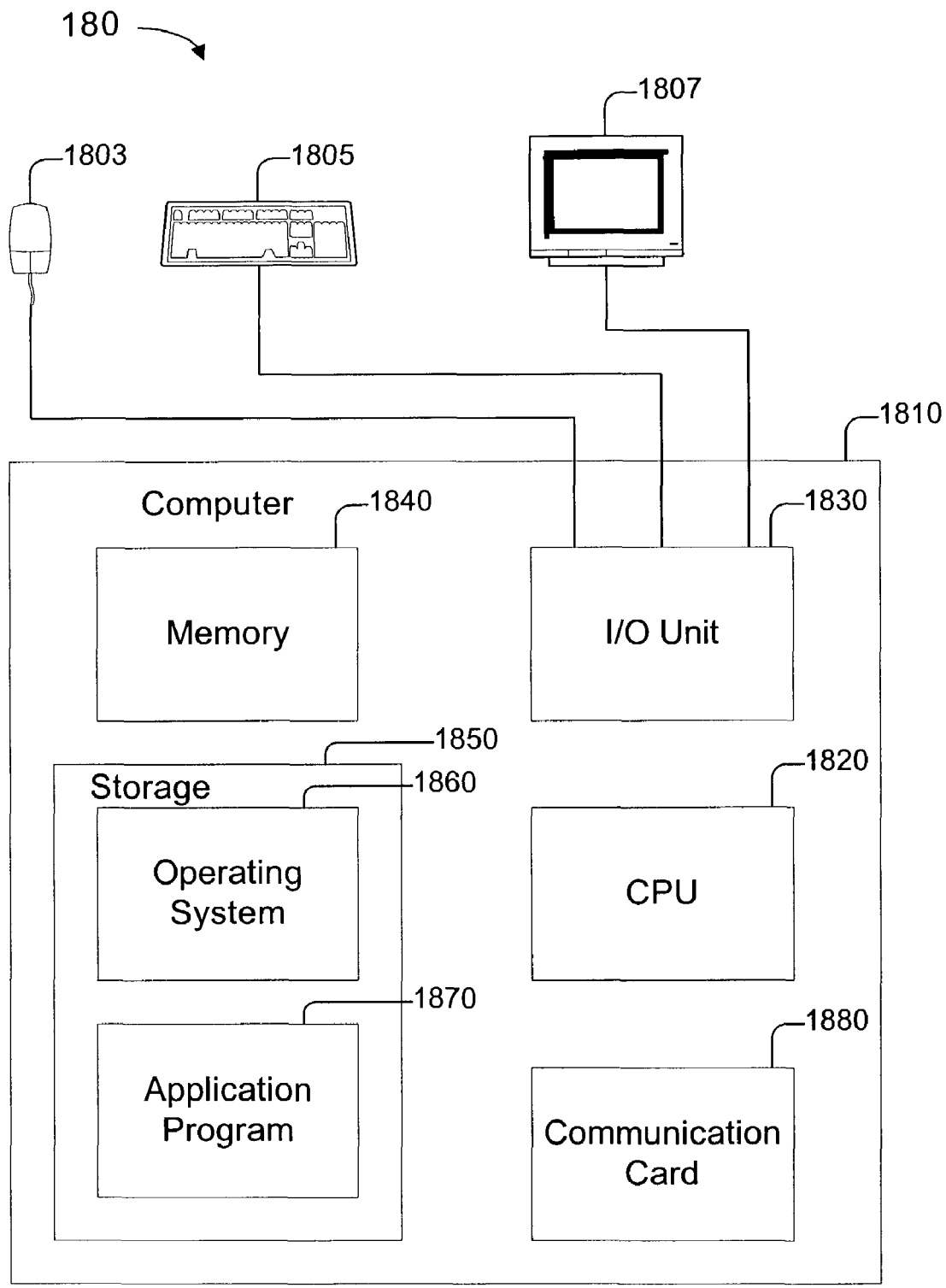
FIG. 2 is a block diagram of a computing device from the communications system of FIG. 1.

Referring to FIG. 2, exemplary computing device 180 includes one or more hardware components and one or more software components. More specifically, computing device 180 includes various input/output (I/O) devices (e.g., mouse 1803, keyboard 1805, and display 1807) and a general purpose computer 1810 having a central processor unit (CPU) 1820, an I/O unit 1830, memory 1840, and storage 1850 that stores data and various programs such as operating system 1860 (e.g., DOS, Windows®, Windows® 95, Windows® 98, Windows® 2000, Windows® NT, Windows® Millennium Edition, Windows® XP, OS/2®, Macintosh OS, and Linux) and one or more application programs 1870. Computer system 1810 also typically includes some sort of communications card or device 1880 (e.g., a modem or a network adapter) for exchanging data with a communications network (e.g., communications network 150 of FIG. 1).

Examples of application programs 1870 include authoring applications (e.g., word processing programs, database programs, spreadsheet programs, presentation programs, electronic mail programs and graphics programs) capable of generating documents or other electronic content, browser applications (e.g., Netscape's Navigator and Microsoft's Internet Explorer) capable of rendering standard Internet content, personal information management (PIM) programs (e.g., Microsoft® Outlook®, Outlook® Express, and Lotus Notes®) capable of managing personal information, and other programs (e.g., contact management software, time management software, expense reporting applications, and fax programs).

Referring again to FIG. 1, the communications network 150 typically includes a delivery network making direct or indirect communication between the patients 110, medical personnel 120, medical imaging personnel 130, and organizations 140, irrespective of physical separation. Examples of a delivery network include the Internet, the World Wide Web, WANs, LANs, analog or digital wired and wireless telephone networks (e.g., public switched telephone network (PSTN), integrated services digital network (ISDN), and various types of digital subscriber lines (xDSL)), radio, television, cable, satellite, and/or any other delivery mechanism for carrying data.

The electronic data stores 160 includes one or more databases that contain electronic information related to information flow data and workflow data in medical imaging services. In addition, different imaging tests, their measures and results can also be input and modified using standard formats and data fields. The example used here is a nuclear cardiology imaging services, and the test example with gated SPECT (single photon emission computerized tomography) imaging.

The servers 170 and 175 may include different types of servers such as a web server and/or a database server. The servers 170 and 175 may host the one or more of the electronic data stores 160. The servers 170 and 175 also may host a web-accessible interface that enables the patients 110, medical personnel 120, medical imaging personnel 130, and organizations 140 to exchange data with the electronic data stores 160 using the communications network 150. The electronic data stores 160 and the servers 170 and 175 enable the different people and groups of people to access and exchange data related to information flow and workflow in medical imaging services simultaneously and in substantially real-time. For example, the servers 170 and 175 may host a website (e.g., a secure website) that is programmed to interface with the electronic data stores 160. The website may be accessed by the patients 110, medical personnel 120, medical imaging personnel 130, and organizations 140 through communications network 150 using, for example, a browser application.

In the implementation of FIG. 1, the electronic data store 160 includes multiple modules that perform various functions in the management of workflow and information flow in medical imaging services. For example, the electronic data store includes a processes/steps module 161, a personnel/locations module 162, a performance metrics modules 163, and an analysis tools module 164. In one implementation, the different modules are fully integrated and interactive with each other. The processes/steps module 161 and the personnel/locations module 162 include the functions of the database dedicated to the workflow and information flow process and the specific steps of the various processes among the different personnel in different locations. These functions include presenting graphical user interfaces through a server (e.g., servers 170 and 175) to track and monitor individual patients throughout the medical imaging process as the patient first visits, for example, a primary care physician and the activities at the primary care practice through referral to a medical imaging center, and as the patient participates in follow-up care. The modules 161 and 162 provide functionality to track a dataset for all individuals at different locations, their activities through the entire imaging service process and at the same time provide the functionality to accumulate and aggregate data for multiple datasets over a period of time in the database, which can be used by the other modules (e.g., performance metrics module 163 and analysis tools module 164).

The performance metrics module 163 provides the functionality for manipulating the data received to calculate various flow metrics related to the workflow and information flow process. These calculations include measurements of multiple different points in the workflow and information flow process that provide objective statistics that can be used to analyze the interaction of the workflow process with the information flow process.

The performance metrics module 163 also provides the functionality for manipulating the data received to calculate various outcome metrics, such as, for example, diagnostic testing outcome metrics, clinical outcome metrics, service outcome metrics, and financial outcome metrics.

The analysis tools module 164 provides the functionality to perform a series of practical and business performance analysis, which may combine the information from the other modules to present modifiable, flexible and user friendly reports on various aspects of the overall process.

Each of the modules and their functionality are described in more specific detail below.

A secure website is a website that includes some measure of access controls and requires some level of authorization to interact with the website. Different levels of access may be granted to different users and the access may be segregated such that different users can only access different portions of the website and/or only may be authorized certain levels of access to different portions of the website, such as a read-only type access.

One or more of the computing devices 180 and 185, the electronic data stores 160, and the servers 170 and 175 may be physically located at locations different from those illustrated in FIG. 1.

The patients 110, medical personnel 120, medical imaging personnel 130, and organizations 140 typically are located in different physical locations from each other. For example, patients 110 may access the communications system 100 from their home, the medical personnel 120 may access the system from physicians offices and/or hospitals, clinics or the like, medical imaging personnel 130 may access the communications system 100 from imaging centers, and organizations 140 may access the system from organization facilities. These people and groups of people may be considered remotely-located components with respect to other components of the communications system 100, such as electronic data stores 160 and servers 170 and 175, which may be considered centrally-located components. It is possible that a centrally-located component may be physically located near a remotely-located component and still maintain the same logical relationship as if the components were not physically located near each other. Thus, as described above, even though the different users or groups of users may be located in different locations, the users may access exchange data and communicate with components and information maintained at the central location by using a browser application that access a website that interfaces with the electronic data store.

One or more firewalls 190 may be used to prevent unauthorized access to the different components of the communications system 100. The firewalls 190 may include firewalls that are located at the particular component or installed on a particular component and/or may include firewalls that are remotely located from the components and through which communications must pass. The firewalls may include hardware and/or software firewalls.

The network and data store systems include security administration functionality such as using logon codes and different level of access such that, for example, patients and referral physicians cannot modify test results which only can be modified by testing physicians.

2. Mapping of Processes and Steps

Figure 3:
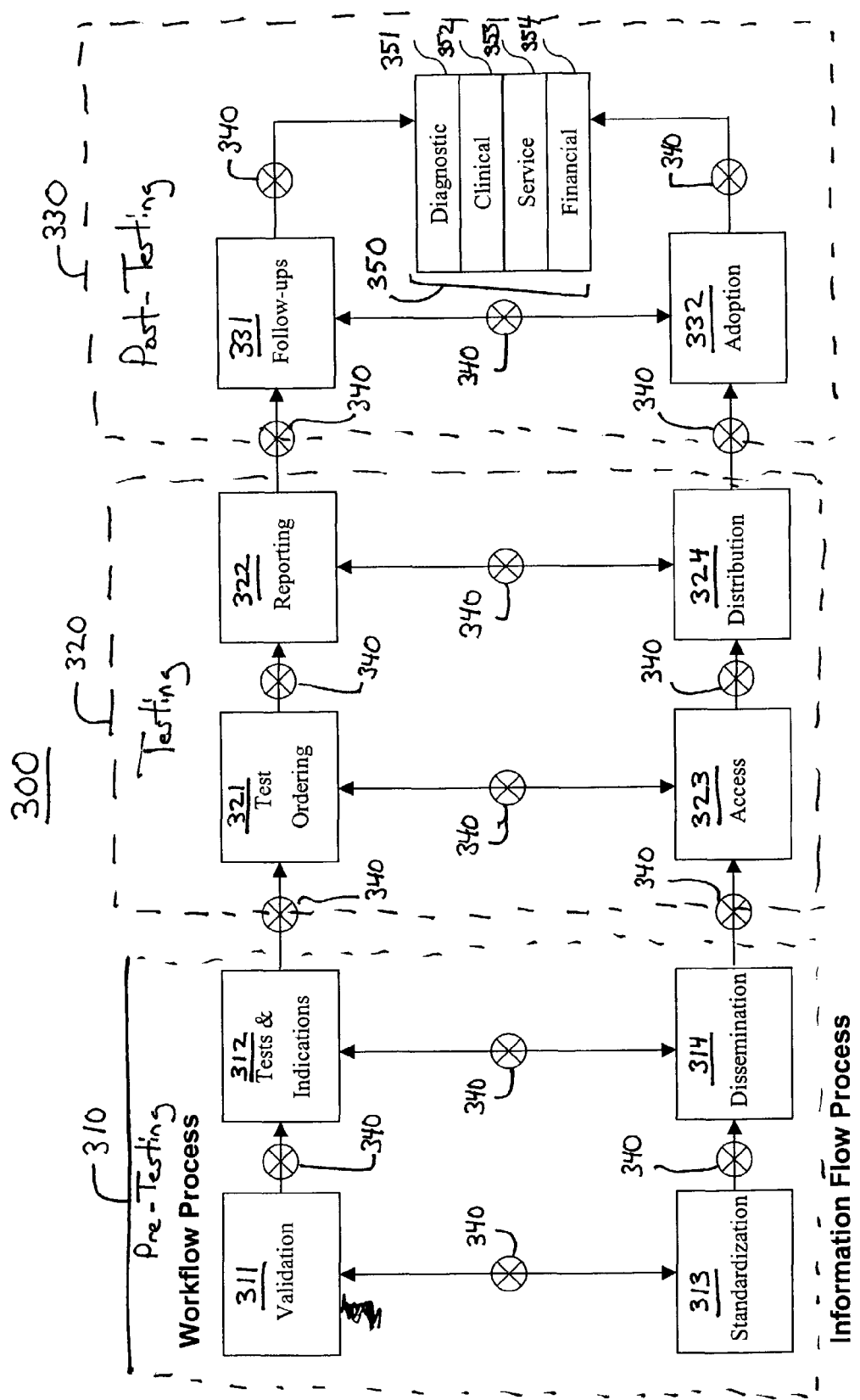
FIG. 3 is a flow chart of an exemplary process for managing information flow and workflow in medical imaging services.

Referring to FIG. 3, process 300 illustrates that the process is mapped as the workflow process and the corresponding information flow, and these processes are further mapped as specific steps in medical imaging services. Process 300 tracks both the workflow process, which includes the interactions in who (e.g., among different users such as patients, medical personnel, medical imaging personnel, and organizations), what (e.g., activities in a step of the process), when (e.g., time and sequence of the activity), and where (e.g., locations). The information flow process, which includes the information that may be obtained from different workflow interactions among the different user (e.g., the how and the why of the processes). Process 300 has three phases including a pre-testing phase (step 310), a testing phase (step 320), and a post-testing phase (step 330). The pre-testing phase (step 310) includes the workflow and information flow steps that generally occur prior to medical tests being ordered and given to a particular patient. The testing phase (step 320) includes the workflow and information flow steps that generally occur when a particular medical test is ordered and given to a particular patient. The post testing phase (step 330) includes the workflow and information flow steps that generally occur after a particular medical test has been ordered and given to a particular patient. Points 340 mark points in the process where measurements were taken in a previous step.

In the pre-testing phase (step 310), the workflow process includes validation (step 311) and tests and indications (step 312). The information flow steps, which parallel the pre-testing phase workflow steps, include standardization (step 313) and dissemination (step 314).

Validation (step 311) includes information that is entered into the electronic data store regarding medical standards, such as, for example, practice and clinical guidelines and relevant medical standards. For example, practice guidelines are guidelines that typically have received professional acknowledgement, peer review, and organizational approval. Clinical practice guidelines are guidelines that typically have received expert consensus and may be accepted as national and/or local guidelines. Other types of validation information include new medical developments such as evidence-based practices, results of randomized clinical trials, and other new medical processes and technologies. The level of authority, such as the American College of Cardiology, the data of publication, the source of access, such as the name and issue of a journal or URL, also may be entered into database.

Validation (step 311) also enables medical guideline and knowledge management, such as, for example, including a guideline list; incorporating new guidelines; updating guidelines and new indications; updating/creating new guidelines in the database including name of guidelines, organizations, publication resources and date, and a URL for linking to the text of the guideline. Other guideline and knowledge management includes the ability to update indications in a manner that incorporates a flexible modification of both test indication with review of the current indication list (to see if it exists now), new indication name, indication category (such as history, ECG, symptoms, arrhythmia, known coronary disease, MI, risk stratification, treatment and intervention), ICD code, reimbursement status with color codes; update reimbursement status; indicated/reimbursed (red); indicated/not reimbursed (blue); not indicated/not reimbursed (black); guideline compliance; compliance vs. non-compliance; patient outcomes in certain populations; difference in local outcomes vs. national predictions; and providing established clinical practice guidelines and indications for appropriate and inappropriate testing to primary care providers as referral expert resources.

Tests and indications (step 312) include information relating to different imaging tests and procedures, risk assessment and test applications (e.g., pre-testing patient risk assessment based on clinical information using an established model, the need for an imaging test for further risk stratification based on standards or guidelines, such as a specific test indicated or not indicated for a specific patient with specific medical histories, diseases, or symptoms). Tests and Indications (step 312) also includes embedding risk assessment applications in the program using established risk scoring algorithms and/or models.

The information relating to validation (step 311) may be entered into the database and used to determine particular information flow metrics when compared against the validation related information, such as flow metrics related to standardization (step 313). One measure of standardization (step 313) includes the time it takes from the date of publication of a medical standard until the standard is incorporated into routine patient care practice.

Standardization (step 313) in information flow process includes, for example, information about the time of standards publication and the time applied to a given patient, availability of a standard in an imaging center, and the level of authority of the standard.

Dissemination (step 314) in the information flow process includes the time of risk assessment and indication of a test applied to a patient.

In the testing phase (step 320), the workflow process includes test ordering (step 321) and reporting (step 322). Test ordering (step 321) and test reporting (step 322) includes the data that may be obtained when a patient visits a physician's office, a clinic, or a hospital, and the data that is obtained from a medical imaging center when the patient is sent as a referral from the initial visit to the physician, clinic, or hospital. The information flow steps, which parallel the testing phase workflow steps, include access (step 323) and distribution (step 324).

More specifically, for example, test ordering (step 321) may include patient scheduling, prioritizing, test selection and protocol selection.

Test reporting (step 322) may include test results classification, such as normal or abnormal, post-testing risk classification, such as low, intermediate or high risk, results delivery status, and results reception level, such as understand it, not understand it or more questions.

Access (step 323) may include time of a referral physician access imaging center for scheduling and prioritizing a patient for a test, selection of tests and protocols.

Distribution (step 324) may include time of the test results delivered to referrals from imaging center, and the time of risk classification from the patient symptom presentation.

In the post-testing phase (step 330), the workflow process includes follow-ups (step 331) and the parallel information flow step includes adoption (step 332). The follow-ups (step 331) includes data that may be obtained following the testing period, such as data and information obtained from follow-up visits to the primary care physician as well as direct input from the patient.

More specifically, for example, follow-ups (step 332) may include the impact of test results to this patient clinical management and further work-up and specialty physician consultations.

Adoption (step 331) may include the time to change a patient clinical management or seeing a specialty physician based on the results.

The post-testing phase (step 330) also includes outcomes (step 350), which are the culmination of the data obtained throughout the workflow and information flow processes as the results of both flow processes to become outcome metrics for performance measurements. The outcome metrics (step 350) includes diagnostic outcomes (step 351), clinical outcomes (step 352), service outcomes (step 353), and financial outcomes (step 354).

Diagnostic outcomes (step 351) may include feedback from patient and referral physicians regarding the patient clinical correlations after making the diagnosis from a test, test accuracy compared with other further testing, and any intervention and surgery led by the test.

Clinical outcomes (step 352) may include patient symptom and changes feedback from patients themselves and their referral physicians, functional measurements and changes from testing over time, and clinical events.

Service outcomes (step 353) may include service satisfactions related to personnel and service steps in the imaging service.

Financial outcomes (step 354) may include billing and reimbursement status.

These measurement examples of the processes and its steps will be illustrated on Process Metrics.

3. Data Collection and Tracking

At various measurement steps of process 300, such as throughout the process, measurements may be taken to assist in objectively quantifying the workflow and information flow processes. The information obtained at the various measurement steps may be used to calculate the process metrics, which may provide specific information flow metrics and outcome metrics that relate to a particular step in the process and/or to portions of the process and/or the workflow process as a whole. The different types of metrics are discussed in more detail below.

Additionally, the data that is obtained at the various steps and measurement points may be communicated to the central electronic data store and server location by different users in different locations at different dates in the network. The different users (e.g., patients 110, medical personnel 120, medical imaging personnel 130, and organizations 140 of FIG. 1) may enter the data obtained at the various into a computing device (e.g., computing devices 180 and 185 of FIG. 1) that communicates and exchanges data with the other components of the communications system 100 of FIG. 1. In one exemplary implementation, the different users access the electronic data store 160 and the servers 170 and 175 using a browser application to provide data input to these components by accessing a secure website that interfaces with the electronic data store 160.

Referring to FIGS. 4-21, exemplary screen shots illustrate different screens of a graphical user interface presented to the different users during the workflow process through a browser application that allows the users to interface and interact with the database. Data is collected through the graphical user interface and used to calculate the various different metrics.

Figure 4:
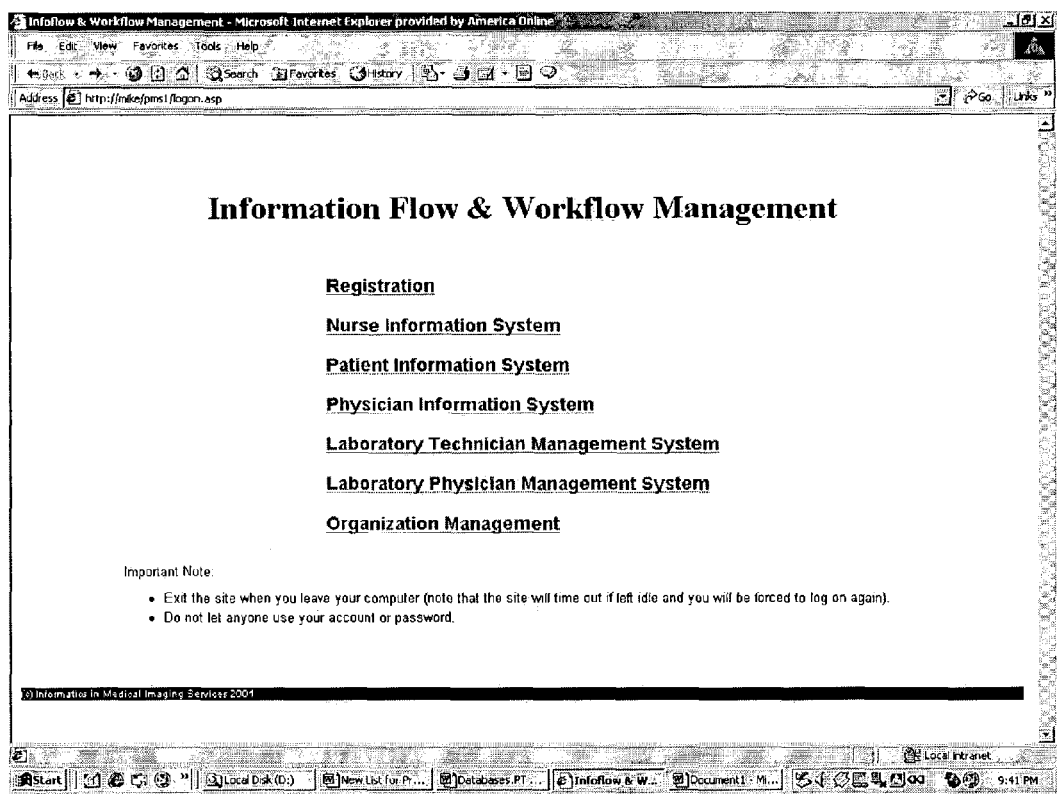
Figure 5:
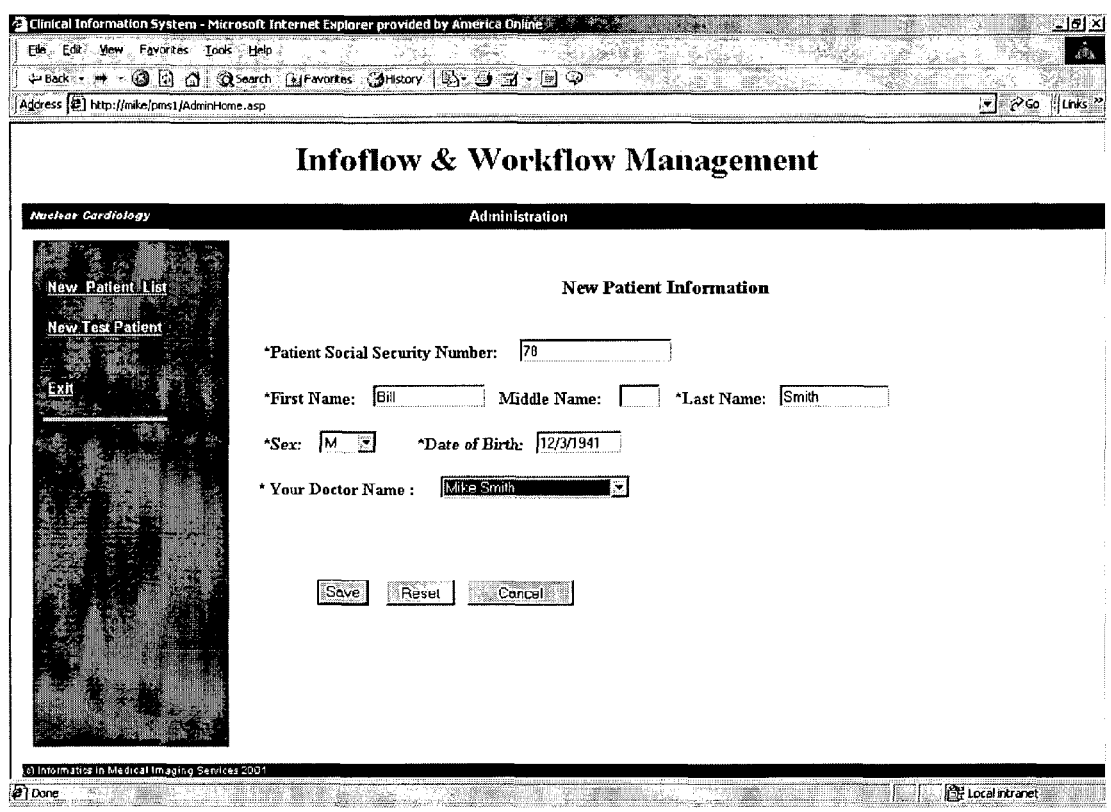

FIG. 4 shows a screen shot 400 of a login screen and provides an indication of the links to the different systems available to different personnel. FIG. 5 illustrates a screen shot 500 of a registration screen for a new patient that enables input of patient demographic information into the system. For example, the demographic information may be taken and input by a registrar in a physician's office.

Figure 6:
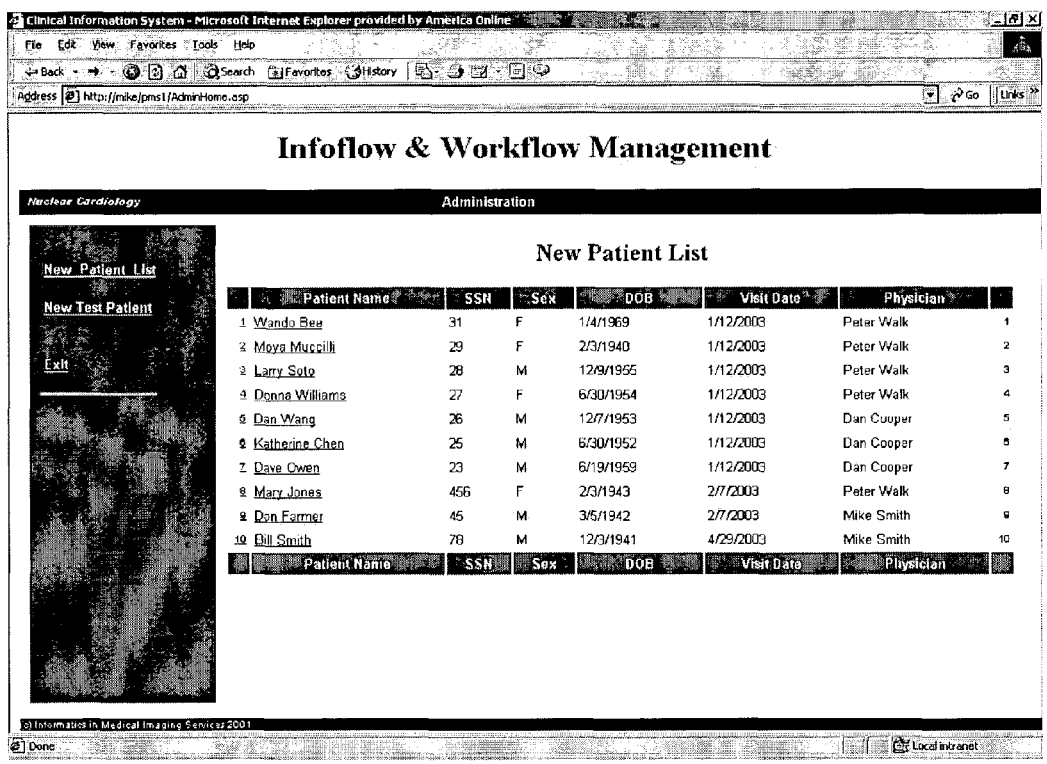
Figure 7:
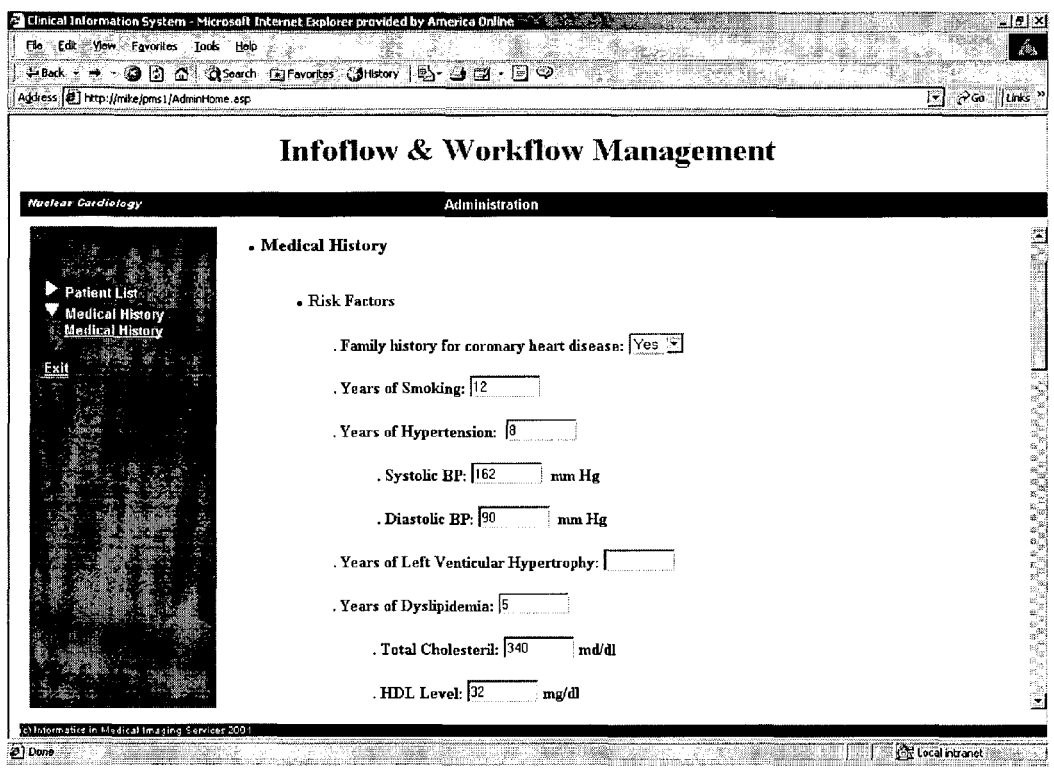

FIG. 6 shows a screen shot 600 of a new patient list that may be presented to a nurse in the physician's office. The nurse may select one of the patients from the list to access additional screens related to that particular patient. For example, FIG. 7 illustrates a screen shot 700 that shows the top part of a medical history form that may be used to enter medical history data for a particular patient. Information that is entered into the system is stored and may later be accessed by other authorized personnel. For example, the medical history information may be taken by a nurse using the nurse information system and then saved for accessing later by a physician using the physician information system. For returning patients, the filled-out forms may be presented to the personnel and may be updated as necessary.

Figure 8:
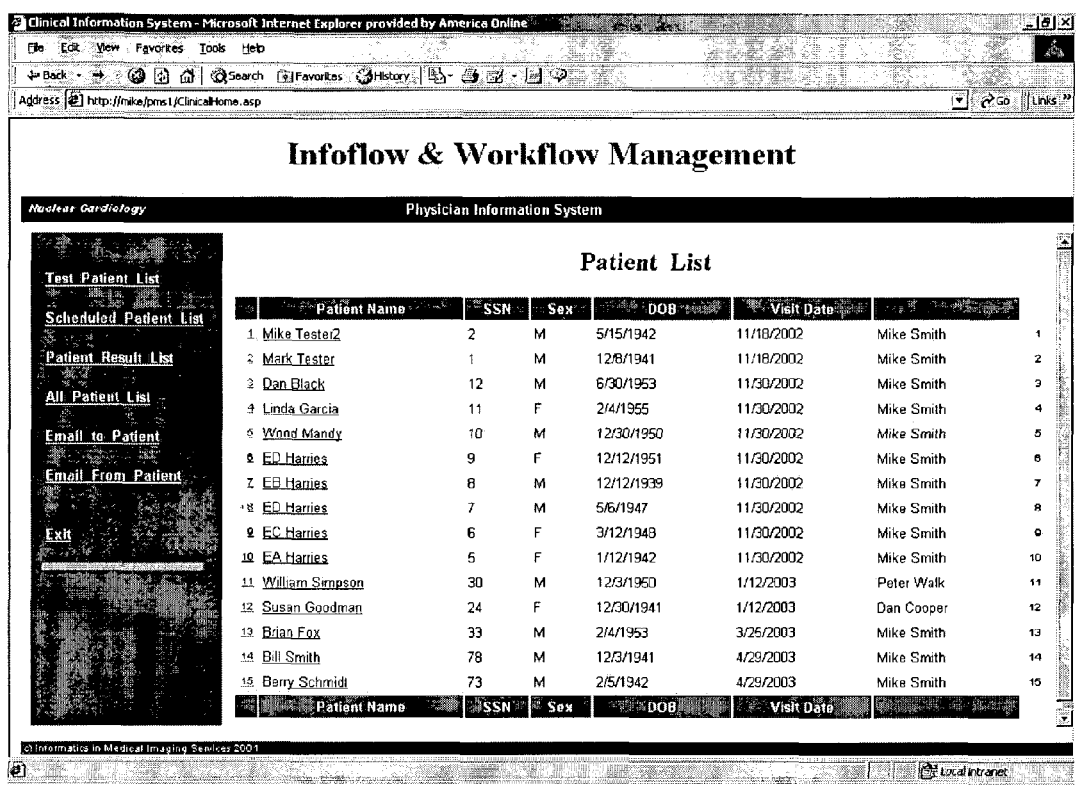
Figure 10:
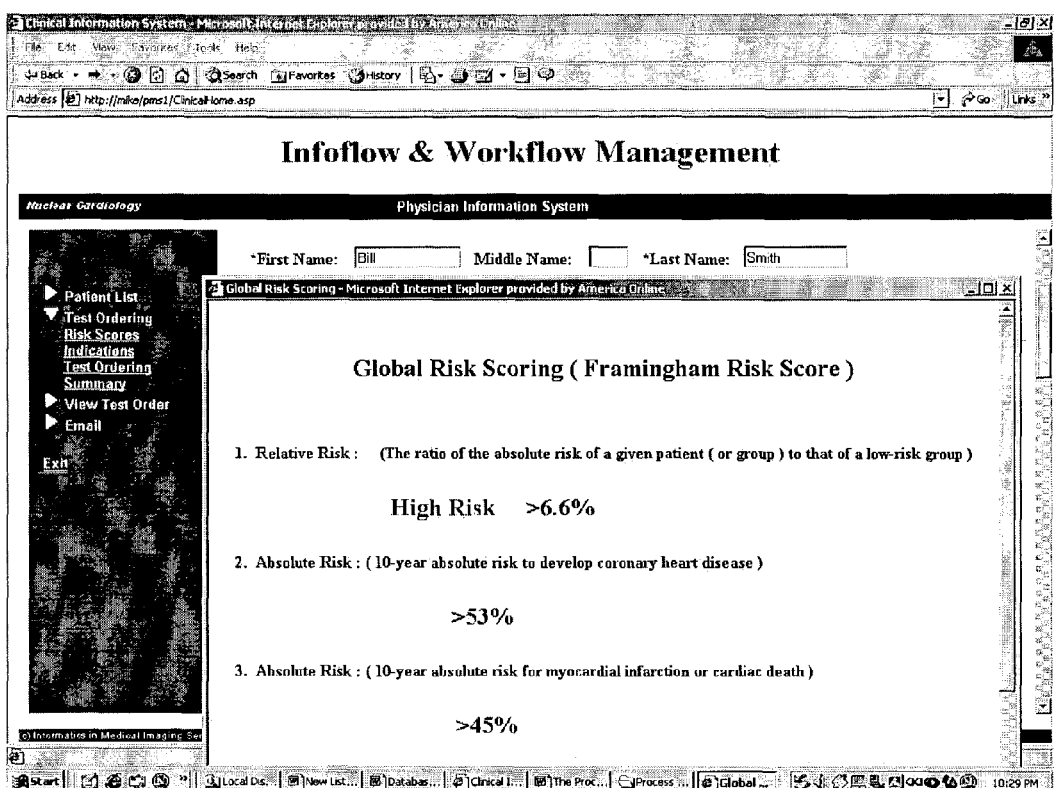

FIG. 8 shows a screen shot 800 that provides a list of patients to the physician. The physician may select one of the patients from the list to access additional screens related to that particular patient. For example, FIG. 9 illustrates a screen shot 900 that provides global risk scores based on the medical history information taken previously by the nurse and as may have been supplemented and/or updated by the physician. The electronic data store includes algorithms that take relevant patient information that is entered into the system and can calculate various medical scores based on a particular model. For example, FIG. 10 shows a screen shot 1000 that provides a global risk scoring for a particular patient. The data entered for the patient was applied to a risk model (e.g., the Framingham model) and the appropriate risk scores were calculated. One benefit of the system is to provide risk scoring to the physician at the point of care. Other risk models and algorithms may be used, and the needed information may be collected using the graphical user interface.

Figure 11:
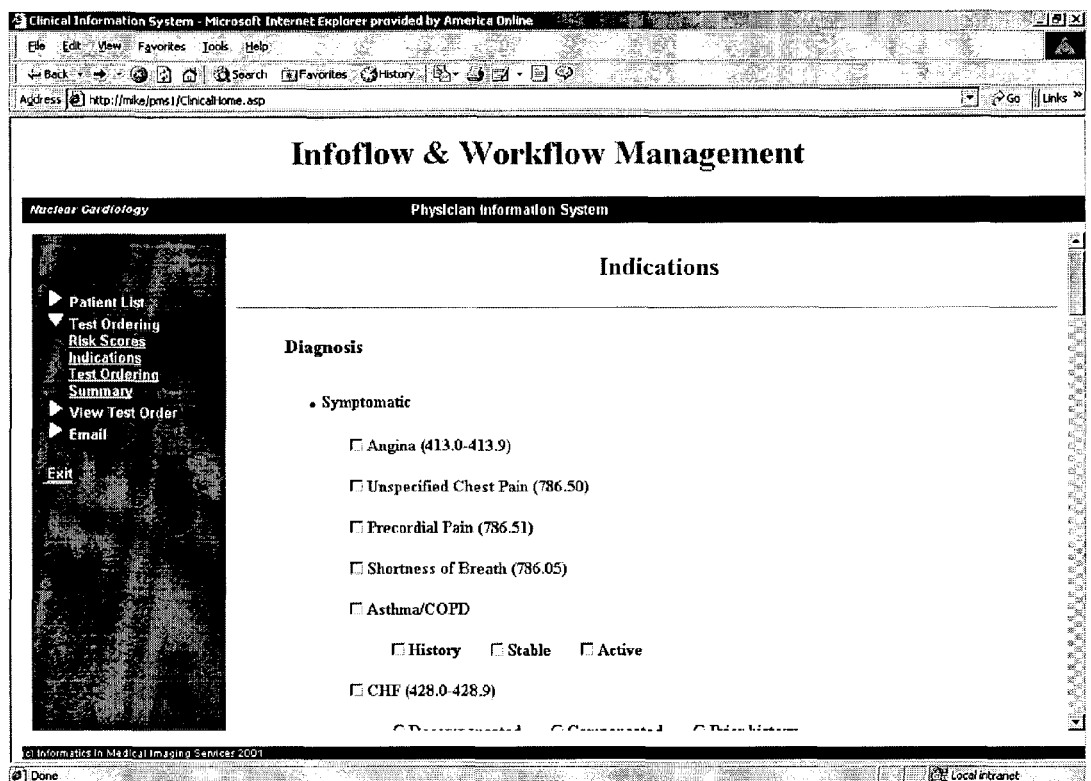

FIG. 11 illustrates a screen shot 1100 of diagnosis information that may be entered by the physician regarding the particular patient. For example, the physician may evaluate the patient's presentation for other indications of any further risk stratification using other testing procedures that typically are referred from a practice, such as a physician's office or hospital.

Following the entering of additional diagnosis information by the physician, the physician may select a "Guideline" button on the user interface. The selection of the Guideline button causes the relevant patient information that has been entered on the previous screens to be compared against one or more known medical guidelines that have been entered as electronic information into the electronic data store. In one implementation, the information from the guidelines may be entered into the electronic data store as a logical set of queries such that the guideline information will determine which other steps should be taken in accordance with a particular guideline if a particular patient presents with certain indications and diagnosis. Hyperlinks to the full text of the guidelines may be provided.

Figure 12:
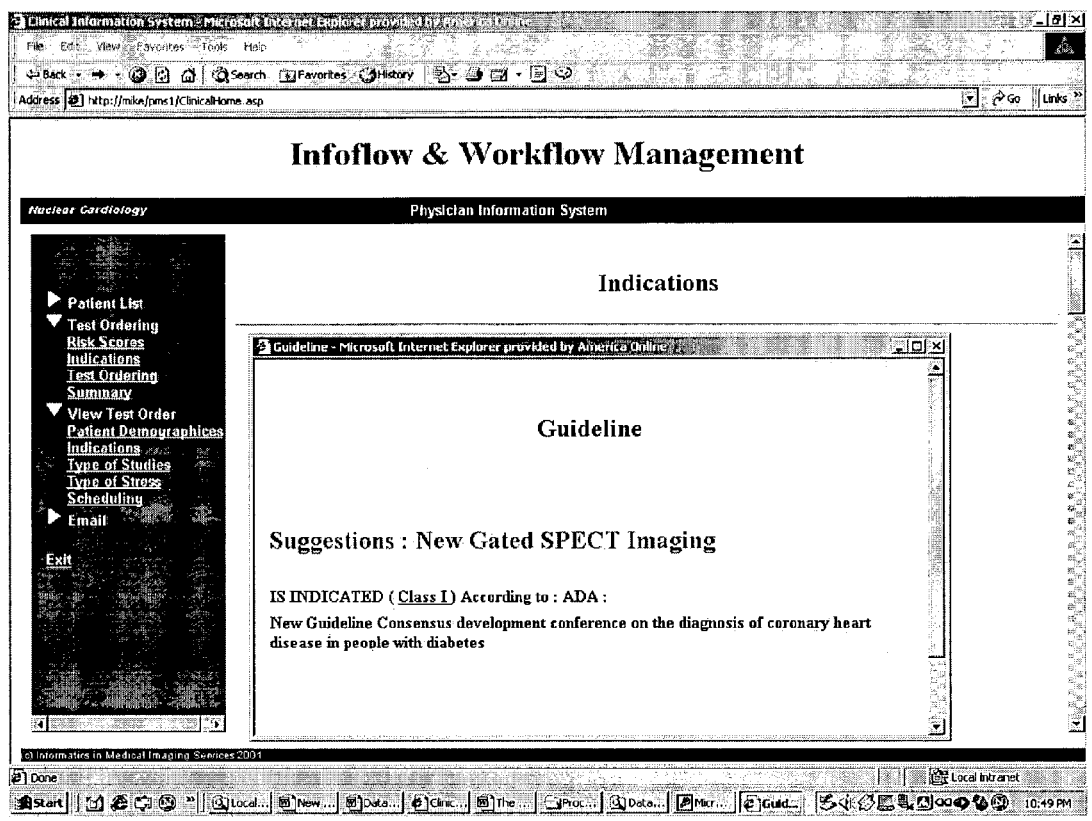

For example, FIG. 12 illustrates a screen shot 1200 of the results of the automatic comparison of the data collected for this particular patient when compared to one or more guidelines. In this example, the results of the comparison of the patient data with the guideline indicates that a further test (e.g., a new Gated SPECT Imaging test) should be performed.

Figure 13:
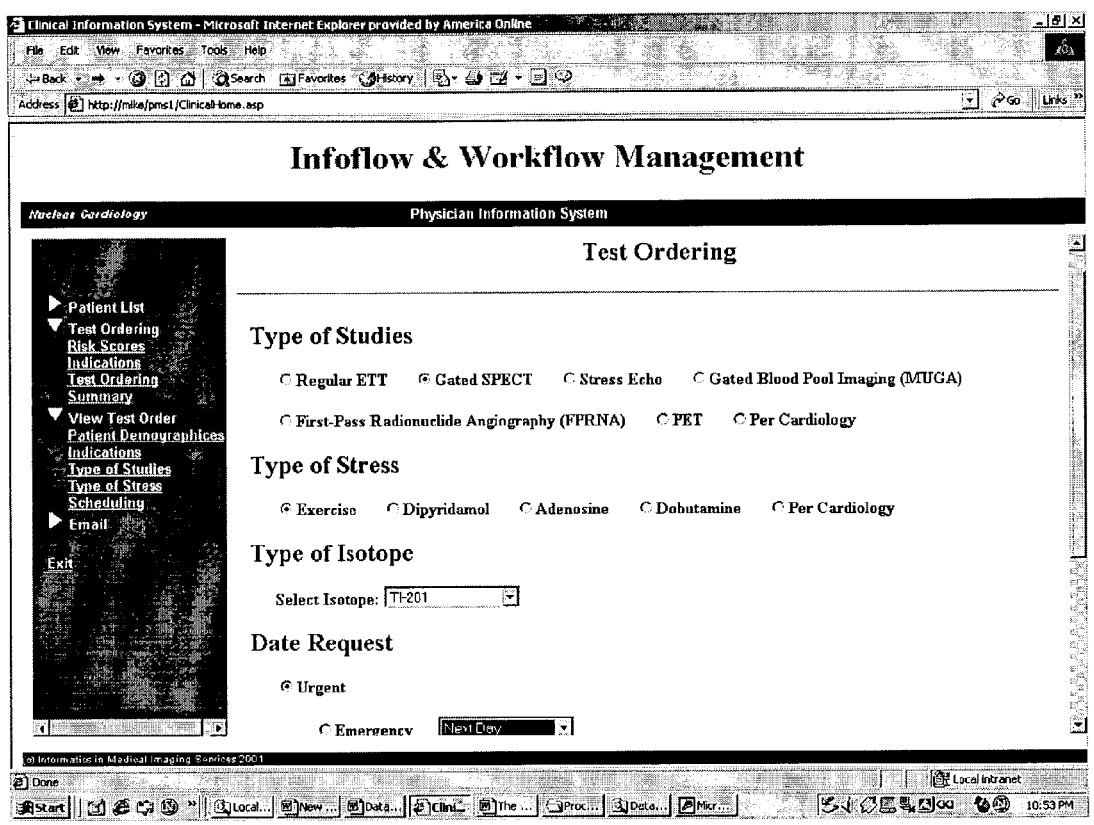

FIG. 13 illustrates a screen shot 1300 that enables the physician to order particular types of tests that may be performed at other locations, such as, for example at a medical imaging center. The physician may order the test, which is then electronically sent to the particular testing center (e.g., medical imaging center) for scheduling.

Figure 14:
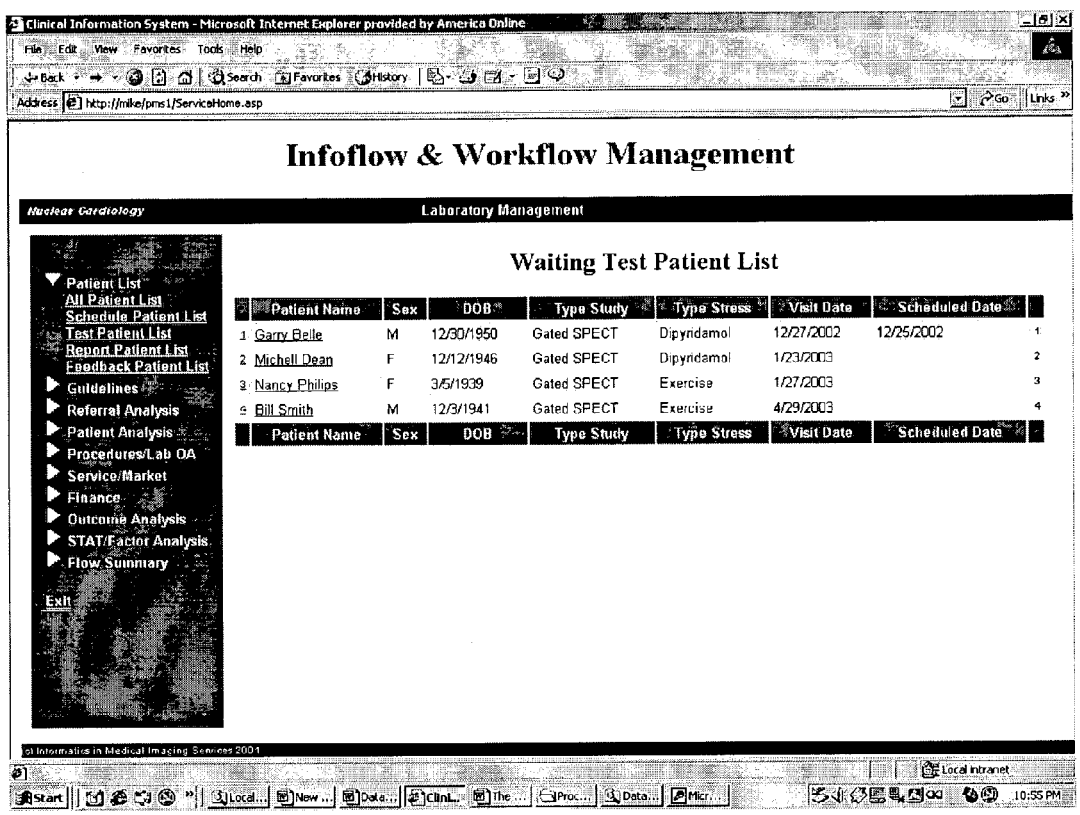
Figure 15:
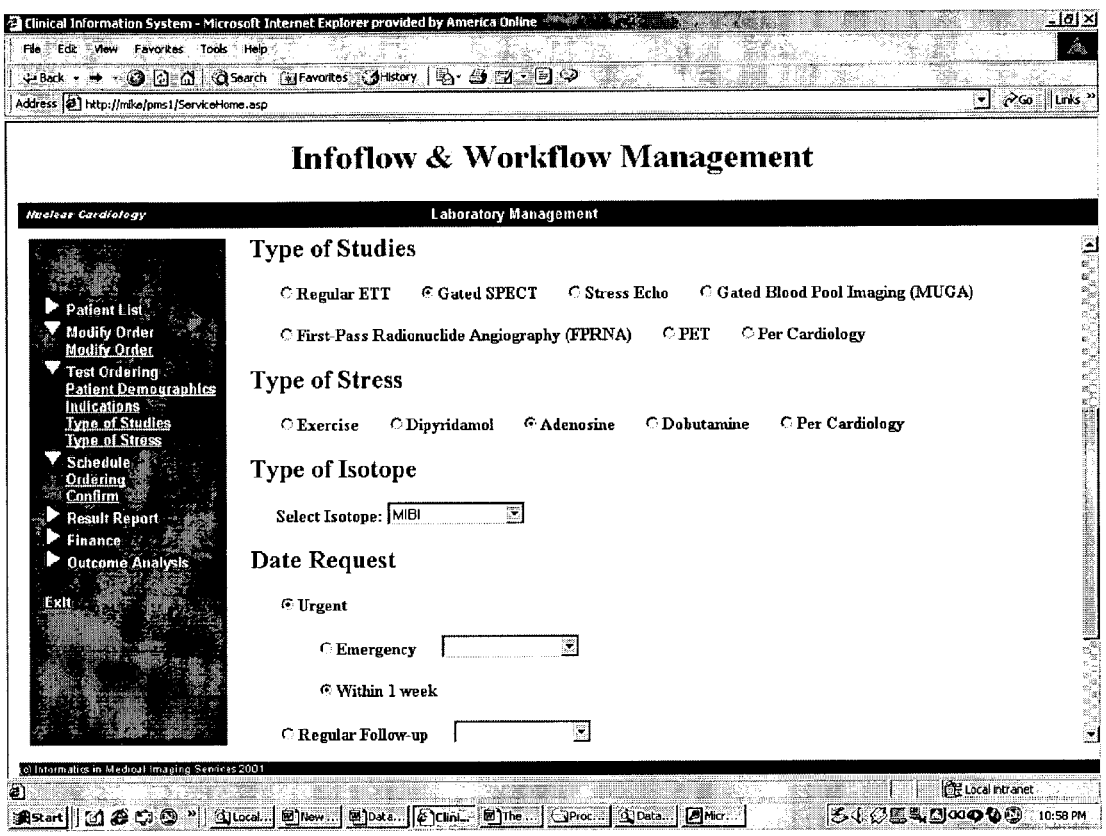
Figure 16:
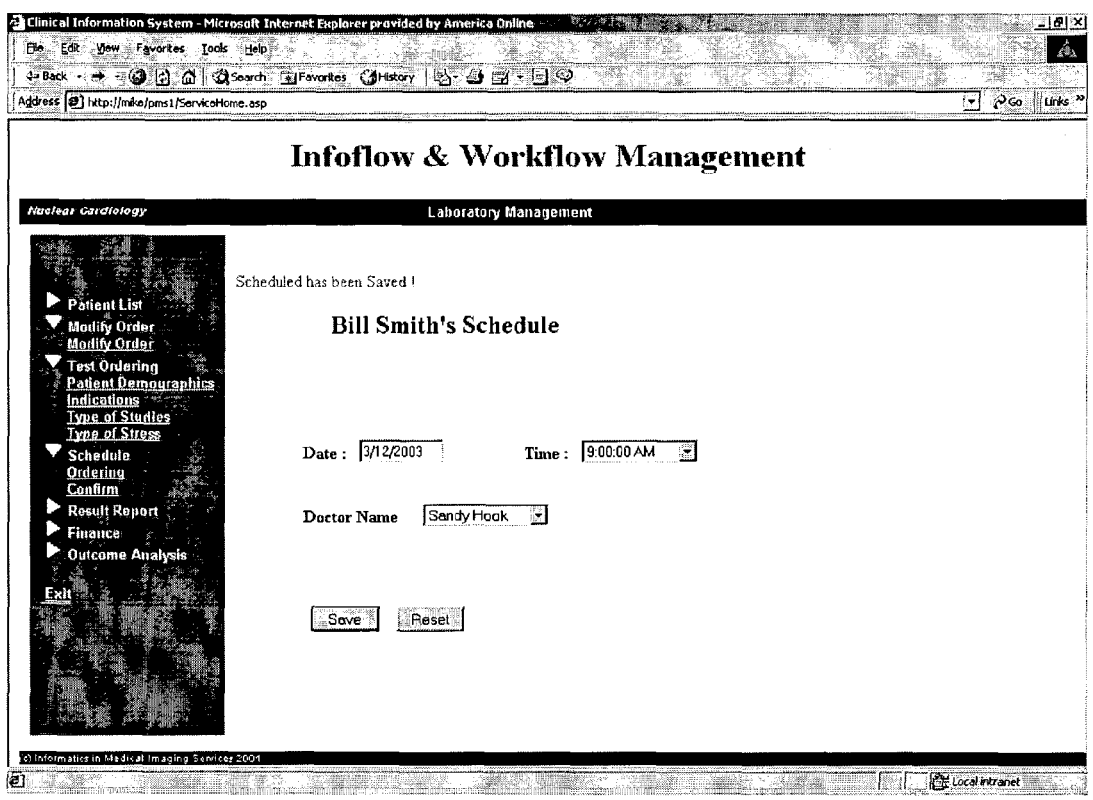
Figure 17:
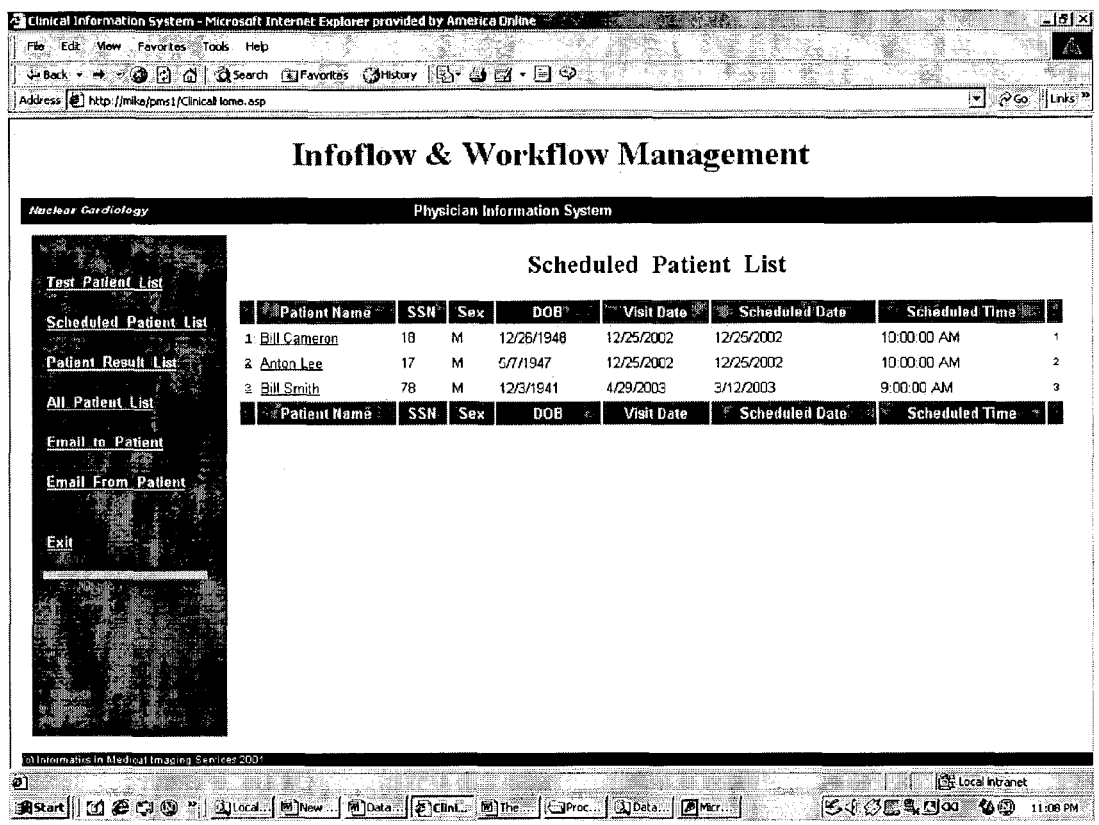

FIG. 14 illustrates a screen shot 1400 that is presented to a lab technician at the testing center. In this example, a list of patients who need testing performed is presented to the technician. The technician and the medical imaging physician (e.g., nuclear cardiologist) can review the patient data entered at the physician's office and make an independent determination as to the type of test that should be performed. Any changes made at the testing center are tracked by the database and can be used in providing feedback to the referring physician as well as providing aggregated data for use in calculating other metrics. FIG. 15 illustrates a screen shot 1500 that enables the testing center to modify the test as ordered by the referring physician. In this example, the type of test may be changed and the type of imaging agents may be changed. FIG. 16 illustrates a screen shot 1600 that enables the testing center to electronically schedule the patient for the test and FIG. 17 illustrates a screen shot 1700 that notifies the referring physician of the scheduled test.

After the test is performed, the test results data may be entered into the electronic data store using the graphical user interface. In one implementation, a lab technician may initially enter the data and the medical imaging physician can later finalize the report. The report may include technical information about the quality of the study, and an interpretation of the results of the test including any likelihood for disease and medical events (e.g., the likelihood of coronary disease and the risk of a cardiac event based on published long-term follow-up study results in similar patient populations).

Figure 18:
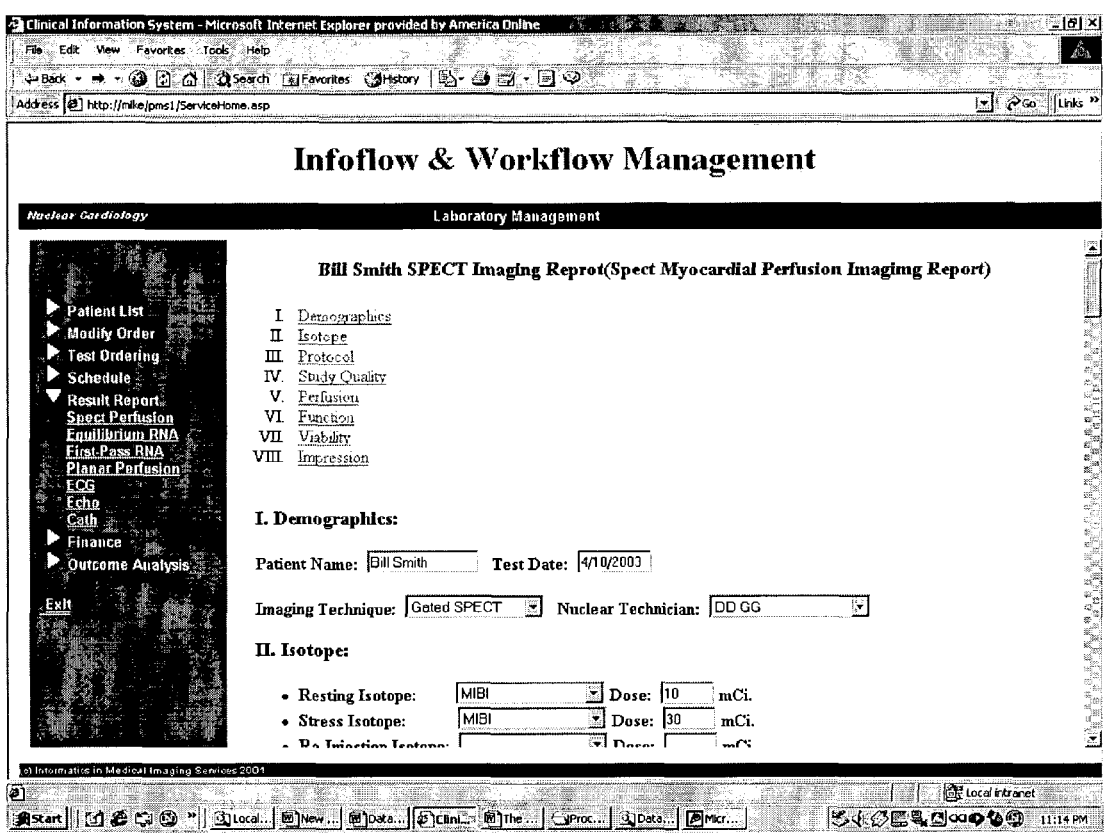

FIG. 18 shows a screen shot 1800 that illustrates the test report. The report may include hyperlinks to different parts of the report. Again, the information is saved and stored at the electronic data store for later access by other users in the process and for calculating different metrics.

Figure 19:
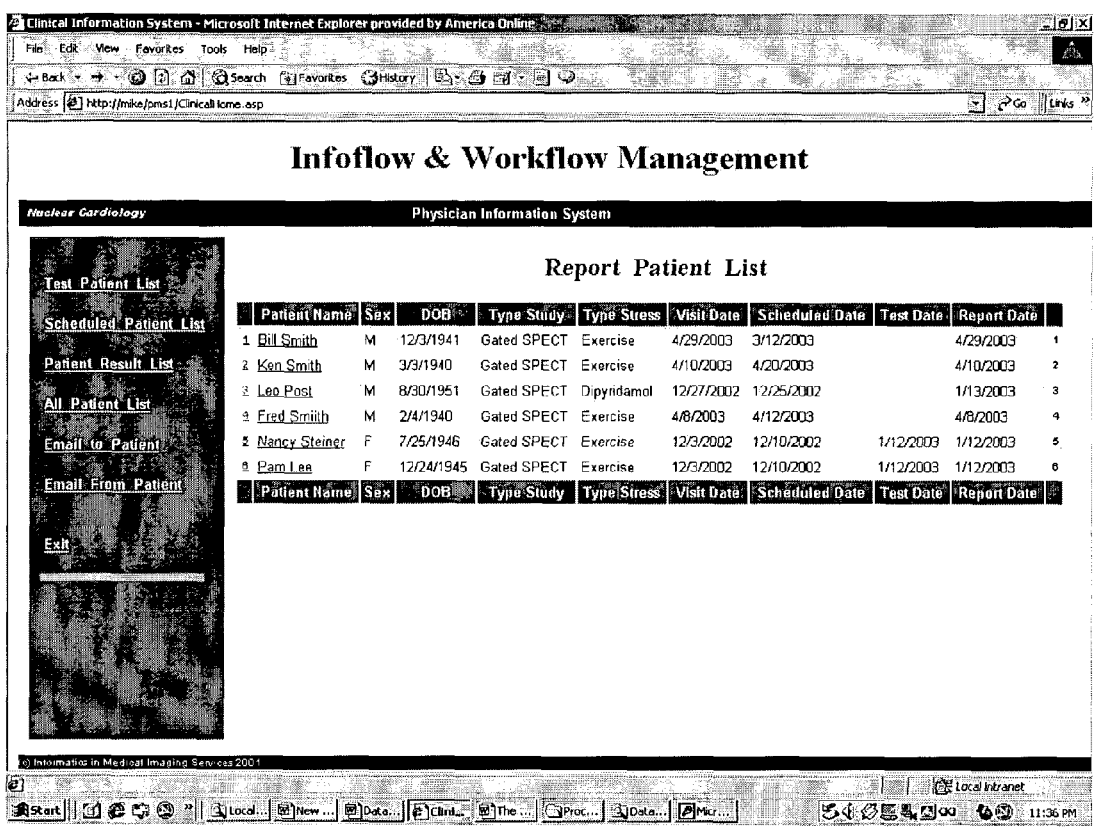
Figure 20:
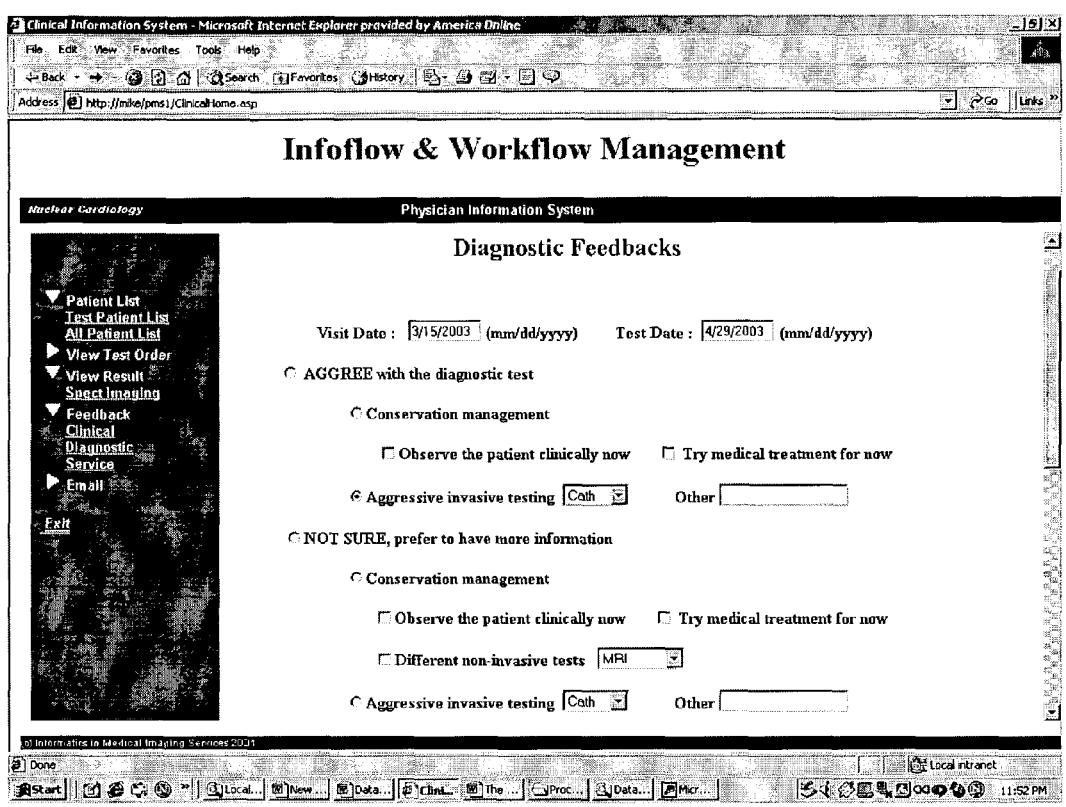
Figure 21:
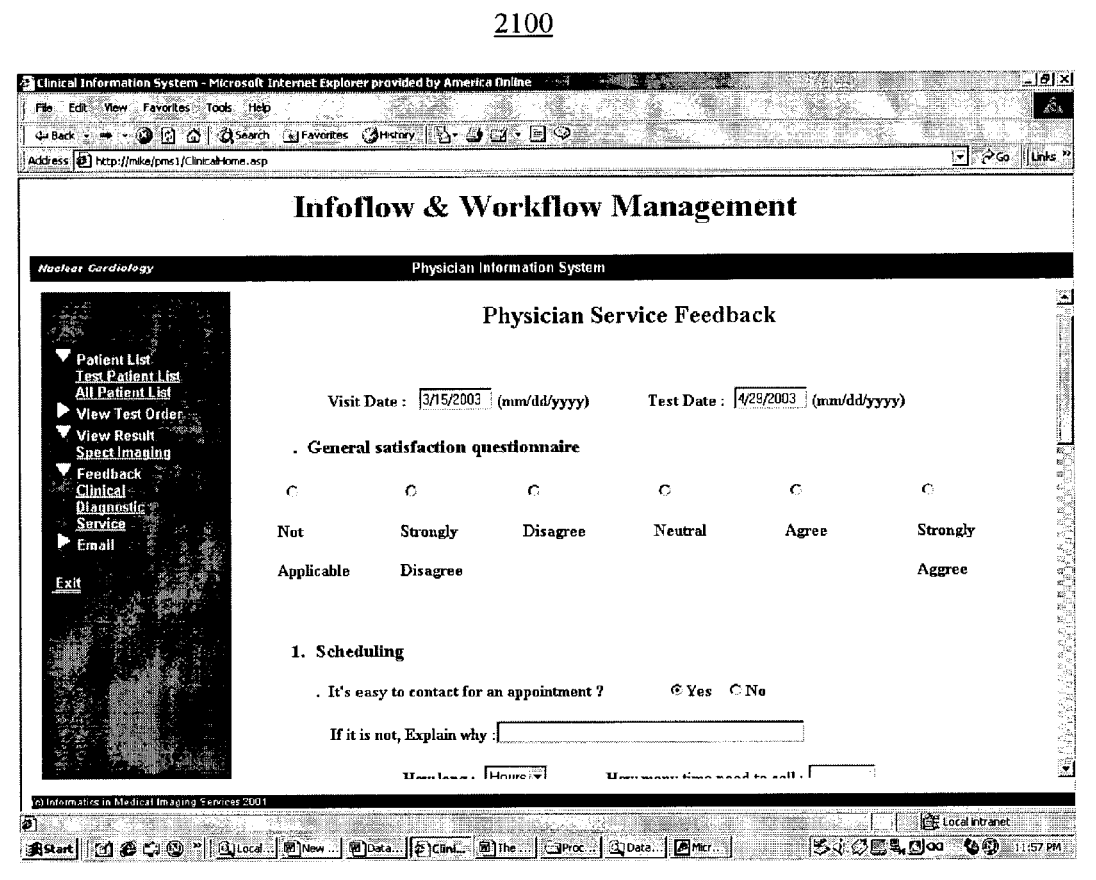

FIG. 19 illustrates a screen shot 1900 that provides a listing of patients that include patients with test results to the referring physician. FIG. 20 illustrates a screen shot 2000 which enables the referring physician to provide additional follow-up data regarding the patient and the testing results feedback, including the physician's clinical opinion of the patient's test results. FIG. 21 illustrates a screen shot 2100 that enables the referring physician to provide service feedback to the medical personnel at the testing center.

The screen shots provided in FIGS. 4-21 are exemplary and other screen shots with other information may be used. Any type of information and data that is typically obtained as part of the medical imaging process may be entered into the system using a graphical user interface. Examples of such information and data include, but is not limited to, patients' input of their demographics, feedback on testing results form variety resources such as other testing centers, from self monitoring device, such as blood pressure and glucose level which can affect the pre-testing risk assessment scoring, clinical events, medications, patient access their own healthcare profiles, pre-test risk scoring, physician's visit, disease management tools, such as information about hypertension and diabetes and communication tools with their physicians and imaging centers.

The system also provide a referral physician a comprehensive patient lists for testing, scheduling, patients with results, input and modification of patient medical history and presentations, pre-test risk assessment using embedded models, access of indications of different tests for different patient populations, application of guidelines input by imaging centers or organizations, ordering different tests and protocols of a test, scheduling and prioritizing patient for tests, communication and feedback with imaging centers, specialty consultations and organizations.

4. Performance Metrics for Assessment of Imaging Services

The data obtained during the workflow process and/or the corresponding information flow process can be used to calculate flow metrics that provide statistics of the who, what, when, where, efficiency and accuracy (the how and why) measurements at different points in the imaging service process. The flow metrics are most useful after a meaningful number of patients have been tracked through the workflow process so that aggregated data may be used to calculate the flow metrics.

Referring also to FIGS. 22 and 23, a table 2200 (FIG. 22) illustrates the workflow statistics and the information flow metrics that may be calculated as part of process 300. Table 2300 (FIG. 23) illustrates a filled-out example of table 2200. In table 2200, patients are abbreviated as "pts."

The data used in tables 2200 and 2300 is obtained during the workflow process, which tracks individual patients through the entire medical imaging process. The data is accumulated and aggregated over time in an electronic data store (e.g., electronic data store 160 of FIG. 1). Reference numbers corresponding to the workflow and information flow step of FIG. 3 are also used in Table 2200 and 2300 to indicate the relationship between the steps in FIG. 3 and the metrics illustrated in the tables.

In table 2300, a query has been run on the electronic information contained within the electronic data store to obtain workflow and information flow data on specific types of patients over a particular time period. In this example, the data used to calculate the statistics in the table comes from patients who presented with diabetes, hypertension, hypercholesterolemia, and were otherwise asymptomatic over the time period from Jan. 1, 2000 to Jan. 1, 2002, which included a total of 2,000 patients.

Table 2300 illustrates the performance of workflow process and information flow process, such as statistics, efficiency and accuracy in these 2,000 patients in an organization. In the Step of Test and Indications (step 312), one can see only 25% of these group of patients did have risk assessment and only 11% referred to gated SPECT imaging. In the corresponding Dissemination step (step 314), it took almost 3 years to reach this small magnitude of implementation of the American Diabetic Association (ADA) recommendations.

However, out of the patient referred, 95% of patients actually need tests for further risk stratification after evaluation by a cardiologist in the imaging center based on guidelines. In the Test Ordering (step 321) and corresponding Access steps (step 323), one can see the difference between referral physicians' selection and actually the tests being done, that the accuracy rate was quite low. In the Reporting (step 322) and corresponding Distribution steps (step 324), the 200 patients' imaging results and results risks were classified. However, it took too long to delivery the results, especially in patients with abnormal scans (50%). In the Follow-up (step 331) and corresponding Adoption step (step 332), post-testing risk were assessed and management plans in majority patients were changes. However, only 50% of abnormal patients were referred for specialty consultations. It took over 3 years to modify management on these patients.

Overview the entire workflow and information flow processes, one can identify the limiting step(s) of the who, what, where, and when using workflow statistics and how and why using the information flow efficiency and accuracy. For example, one can see the critical step with the lowest flow rate is in the Test and Indication step and the reason is low utilization of risk assessment and not further risk stratify those patient. The organization may start to focus on improving understanding of the ADA guidelines in this patient population. As can be seen from the example, other areas in test ordering for referral physicians and reporting for imaging physicians need some improvement as well.

Referring again to FIG. 3, various outcome metrics 350 may be calculated based on the data obtained over a period of time in the workflow and information flow processes. FIGS. 24-28 show exemplary tables that describe the types of outcome metrics that may be calculated.

For example, FIG. 24 shows a table 2400 for various diagnostic outcomes that may be calculated. For instance, the diagnostic outcomes include metrics such as utilization, test accuracy, and clinical correlation. Utilization includes tracking the impact of using a screening test in medical imaging service (e.g., usually non-invasive, such as gated SPECT) on further invasive testing (e.g., validation of the test and decision making for treatment, such as catheterization), interventional therapy (e.g., such as PTCA in patients usually with moderate diseases) and surgery (e.g., such as bypass surgery in patients usually with severe diseases). These measurements can identify the distribution of disease severity in the referred patient population that have undergone the test, the referral physician's practice pattern (behavior), the imaging center, and the organizational standardization and implementation of risk assessment and practice guidelines in their practices.

For example, a referral physician who is too aggressive may send more patients to have more invasive testing performed (e.g., catheterization), including those patients that may not truly require such an invasive test, such as those patients with normal scans. In this case for this particular physician, the invasive testing rate (e.g., the cath rate) in normal (nl) scans will be high. In contrast, a referral physician who is too conservative might refer fewer patients to have invasive tests performed (e.g., catheterization), and the invasive testing rate (e.g., the cath rate) in abnormal (abnl) scans may be low.

If the referred patients only have mild diseases, the use of interventional and surgical therapy rate will be low and, if the referred patients have severe diseases, the rate will be high. The calculations reflect how the referral physicians, organization and imaging center standardize and implement risk assessment and practice guidelines in their practices.

Accuracy includes measurements of diagnostic test accuracies in terms of patients, anatomy (such as location of specific coronary arteries) and comparisons with other non-invasive tests (such as gated SPECT nuclear test vs. Echocardiography or MRI). These measures are the results compared to a gold standard test (such as cath to define coronary disease) in a specific patient population using established and widely used sensitivity and specificity, and in a given patient using Positive or Negative Predictive Value (delete sensitivity and specificity) sensitivity and specificity that are established but not yet widely used in practice. Although these measures are established in clinical trials (such as sensitivity of gated SPECT imaging in patients with chest pain without history of coronary disease is about 85-90% and specificity is about 80-85%), the measures are not readily available in clinical practices to calculate the accuracies with local expertise and interpretations in their specific patient population. Also, it can help physicians to further identify what kind of patients and who the patients are if the testing results are not accurate. These tools can help improve quality assurance.

Clinical correlation tracks the feedbacks from referral physicians to the results of tests on their patients. Sometimes, the test results do not fit with the clinical picture, such as when a patient with chest pain had a normal gated SPECT scan. The referral physician may have responded with uncertainty and indicating that it is necessary to have further testing or consultations. Usually, medical imaging physicians do not have a systematic way to track the diagnostic outcomes if the tested patients are not their own patients. These functions of these measures, along with feedback combined with patient clinical outcomes, serve as a critical tool for their quality improvement in interpretations, patient selection, and communication.

FIG. 25 illustrates a table 2500 for various clinical outcome metrics that may be calculated. For example, the clinical outcome metrics that may be calculated include event rate metrics, symptoms metrics, and testing indices metrics. Event rate metrics track feedback provided to the medical imaging center by patients and referral physicians following the testing. For example, adverse events such as hospitalization, complications, and life threatening events (e.g., myocardial infarction), and death may be tracked. These measures may be coordinated with diagnostic outcomes (as above) for quality control. Testing indexes metrics measure a patient's physiological functions (such as left ventricular ejection fraction, a single best index for prediction of cardiac death acknowledged by most cardiologists). These variables are compared with prescribed treatment to see the improvement or worsening before and after a given treatment.

Symptoms metrics track feedback provided by patients and referral physicians relating to the patient symptom changes (better or worse). The feedback between patients and referral physicians can be compared to identify differences. Those patients with different responses can be flagged and identified for further investigation and follow-up.

FIG. 26 illustrates a table 2600 for various service outcome metrics that may be calculated including, for example, procedure metrics, referral metrics, and satisfaction metrics. Procedure metrics track all procedure utilizations in a given time period (e.g., a week, a month, and/or a year) performed at a particular imaging center, and compare the procedures performed with benchmark and organizational goals as potential or optimal targets. The benchmarks and organizational goals are not fixed and may be changed by a user input to illustrate the effect of different benchmarks and goals.

Referral metrics track referral physician specialties and their practice locations (e.g., by town and zip code) and compare the referrals received at a particular medical imaging center with benchmark and organizational goals as potential or optimal targets. Specific patient populations, such as patients with diabetes, hypertension, and hypercholestrolemia, can be sorted from the database to identify the size of service coverage compared to the benchmark for service performance using local government or epidemiology data or organizational goals to determine the potentials for future service or testing needs in a particular geographic location or from a particular referral physician practice.

Satisfaction metrics track the feedback from referral physicians and patients on their satisfaction with a particular imaging center service such as scheduling, preparation, reporting results, and clerical accuracy.

FIG. 27 illustrates a table 2700 for various financial outcome metrics that may be calculated including, for example, reimbursement metrics, inadequate reimbursement metrics, cost metrics, and cost-benefit metrics. Reimbursement metrics track a total number or percentage of patient for which reimbursement was received in relation to the billing cycle that can be compared to benchmarks to measure the billing performance.

Inadequate reimbursement metrics track the number or percentage of patients for which no reimbursement was received, as well as the reasons and the resources (e.g., the names of insurance companies) for the inadequate reimbursement. The follow-ups on these inadequate reimbursements may be reported for further improvement.

Cost metrics compute overhead costs from different sources in the medical imaging center or organization.

Cost-benefit metrics track the final net revenues and compare them to a benchmark for further comparison to organizational goals to assess the potential future benefits.

FIG. 28 illustrates a table 2800 for various statistical outcome metrics. The table can provide data in the interaction among personnel, locations, process steps and performance metrics for different purposes. The data can be extrapolated to a spreadsheet and used as input for different mathematical analysis and modeling, such as statistical analysis models. For example, the factor analysis shown here is used to identify which clinical variables are the best for risk assessment pretesting. This analysis can help an organization to use more cost effective indices to identify patients with high risk based on clinical history and less expensive tests before using more expensive imaging tests.

5. Analysis Metrics

Referring again to FIG. 1, the analysis tools module 164 is used to calculate a series of practical clinical and business performance analysis. These analysis tools can also help identify the who (personnel), what (tests and indexes), where (locations and process flow steps) and when (time) in the workflow process metrics, and the how and why in the information flow process metrics in the process. The analysis tools module 164 may include some data and metrics that may overlap with previously discussed metrics. However, there are a variety of combinations for the different metrics that may be used for different clinical and business applications for distinct purposes. From the analysis tools module 164, different reports may be generated that are modifiable, flexible, and user friendly.

One aspect of the analysis tools module 164 includes tracking the personnel and locations in the medical imaging service. For example, tracked patient information includes demographics, communications (e.g., phone # and email address), insurance coverage, medical history, labs, diagnostic imaging test results, medications, analysis from risk assessment tools, and analysis from feedback tools to the physician and the imaging center. Similarly, information is tracked regarding the other different users involved in the medical imaging process, such as those described above with respect to the FIG. 1 and the personnel/locations module 162 of FIG. 1.

The analysis tools module 164 also can provide report data regarding patient analysis such as patient selections; patient demographics selected based on variables in the database; medical history analysis regarding certain disease trends in specific populations; presentations; symptoms and clinic/hospital visits; and tests and indexes including tests performed in patients and specific test results with those patients.

The analysis tools module 164 also uses information obtained using the processes/steps module 161, such as the steps of workflow and information flow as well as related performance metrics tracked by the performance metrics module 163 as described above with respect to the flow metrics and the outcome metrics.

The analysis tools module 164 also tracks test and indexes related to medical imaging services, such as the various testing procedures that can be performed in medical imaging service. For example, in nuclear imaging, tests that may be tracked include gated SPECT, planar, first-pass radionuclide angiography (FPRNA), multiple gated radionuclide angiography (MUGA), and others. Testing results from the various tests that may be tracked include their indexes and measurements, such as percent of perfusion defect, left ventricular ejection fraction, and otherwise.

The analysis tools module 164 can report on utilization data such as service market volumes, referral analysis distribution, and the utilization of certain procedures including the volume and distribution of each type of test. Other utilization information that can be calculated includes applications relative to indications (e.g., comparison of tests actually performed with tests guideline recommended to identify under utilization or over utilization); expanding service in underutilized population (e.g., if tests done<recommended); identifying potential opportunities to increase service; comparing medical guidelines to the standard care given for quality improvement of services; clinical outcome in the test for under-utilized patients to see the risk and identify test(s) for risk stratification; admitting new patients using new criteria of applications by organizations; avoiding system abuse in over-utilized population (e.g., if tests done>recommended); identifying current over-utilized tests and patient populations; evaluating cost effectiveness of a given technology and its application on certain patient populations; and recommending avoidance of over testing in specific test and patient populations using new criteria of applications by organizations.

The analysis tools module 164 also can provide report data regarding referral analysis, such as referral analysis distribution; patient selections; referral physicians' specialty, demographics and geography; new leads analysis of referrals (large geographic areas and zip codes); patient service populations and patients with specific disease populations; referral volume and testing procedures; test selections and performance compared their selection with test actually done by specialty imaging physicians; and projected referrals and potential referrals.

The analysis tools module 164 also can provide service and marketing analysis, such as customer service outcomes; customer service clinic outcomes; referral analysis distribution; service map and market capture; potential service areas compared to benchmark or organizational goals (projections); reimbursement: current volume and revenue, projected volume and revenue; referrals in different areas; and epidemiology and patient distributions.

The analysis tools module 164 also provides customer service and relationship management including the supply chain analysis such as, for example, customer service outcomes; customer service clinic outcomes; referral analysis distribution; feedback: clinical monitoring and outcomes; service satisfaction feedback; and the feedback differences between patients and referral physicians.

The analysis tools module 164 also provides clinical risk assessment, integration and management analysis including, for example, patient selection based on risk class; applications in utilization for risk assessment, high risk assessment and test indications; risk assessment and management for pre-testing and post-testing; and pre-testing risk stratification that uses clinical variables to quantify risks (below average risk, moderate above average risk and high risk compared to the general population) in certain patients (such as diabetes and hypertension) for clinical outcomes (such as myocardial infarction or death) based on established models (e.g., Framingham model). Other risk assessment analysis includes, for example, a risk classification algorithm that is built in to estimate a given patient's relative risk of developing a disease (such as coronary heart disease), absolute risk of the disease consequences or complications (such as heart attacks) and absolute risk of death (such as cardiac death) in the future (such as 10 years). The application of pre-test risk stratification will give the referral physician an opportunity to evaluate for the need of further diagnostic testing using new technology for better risk stratification in individual patients. The high risk category based on a patient's clinical history may serve as a "red flag" for further risk stratification using a diagnostic testing procedure.

Still other risk assessment analysis includes post-testing risk stratification. A diagnostic test has more accurate estimation of a given patient based on the patient physiology and functions to further assess the risk of the patient into low, intermediate or high risk of cardiac events in the near future (such as the cardiac death or myocardial infarction in 1-2 years). This will serve as a triage tool for clinical management. For example, when a patient with pre-testing high risk has a test with a low risk results, this patient most likely will undergo conservative medical therapy and observation. On the other hand, if a patient with pre-testing above average risk has a test with intermediate to high risk results, this patient most likely will undergo aggressive invasive investigation (such as catheterization) and interventional therapy (such as angioplasty or bypass surgery).

Still other risk assessment analysis includes risk comparison; evaluation of a served patient population for utilization; a list of patients that compares pre-testing risks with post testing risks; comparison of risks with clinical outcomes; outcomes analysis including database analysis of clinical and diagnostic outcomes in certain patients population to assess the predictive accuracy of pre-test model and testing technology; and redefining a new model and technology application to identify problems in the application of pre-test model and testing technology on a certain patient population to better redefine the model and use of the technology or applications.

The analysis tools module 164 also enables behavior analysis such as the organizational process of individual physicians; referral analysis distribution; customer service outcomes; customer service clinic outcomes; referral and practice patterns in certain patient populations; patient outcomes using different strategies; evaluation of behavior (or practice) pattern in individual patients, referral physicians and imaging centers comparing their behavior (adoption of standard guidelines and activities of execution) in the processes of workflow and information flow with the outcomes over time; and using information flow and workflow metrics to measure behavior and monitor behavior change.

The analysis tools module 164 also enables factor analysis such as outcome focused analysis to determine the impact of clinical risks and test indices and to select appropriate cutoff points between population sample size and severity of indices.

The analysis tool module 164 enable local practice analysis metrics for use in developing of local database system to measure and track the degree of standard implementation, the difference of patients and practice between national and local, and modification of local standardization. It can be used in measuring and tracking the degree of implementing national standards and guidelines for quality control, improve insurance reimbursement and monitoring legal protection. The analysis tool also can define the difference of patients and practice between national and local levels for patient population characteristics in disease development, progress and response to treatment as well as patient reception to new technologies and treatment. The analysis tool also can define the difference of practice between national and local level to identify the realistic level of local expertise to the national standards in local practice capabilities and technology requirement. The analysis tool also define the difference of practice between national and local level to identify local practice variation from national criteria and standards in diagnosis and diagnostic accuracies to redefine local standards in local practice or recommend new local practice criteria.

The analysis tools module 164 also enables organizational process analysis such as organizational process analysis in individual physicians; workflow and information flow analysis; identification of limiting step, personnel and service; profile top/bottom for responsibilities and actions for improvements; objective performance quantifications and comparisons; quality assurance for medical imaging labs; performance analysis in comparison with benchmarks; simulation and prediction of modified process outcomes with new organizational goals; and dissemination of new policies/guideline/process through the organization.

Furthermore, the analysis tools module 164 enables cycle analysis, such as analysis of historical data and trends using feedback and outcome to modify steps in the processes; monitoring and enhancing current process or redefining and reengineering new process; clinical cycle management (e.g., clinical questions, testing, diagnosis, follow-up/management and clinical outcomes); revenue cycle management (test indications, ordering, performance, reporting, follow-up and billing, financial outcomes); cost effective cycle analysis (comparing different testing approaches and outcomes in a specific patient population); and simulation of outcomes comparing with benchmarks or organizational projected goals with modification of current steps of processes.

The described systems, methods, and techniques may be implemented in digital and/or analog electronic circuitry, computer hardware, firmware, software, or in combinations of these elements. Apparatus embodying these techniques may include appropriate input and output devices, a computer processor, and a computer program product tangibly embodied in a machine-readable storage device for execution by a programmable processor. A process embodying these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

It will be understood that various modifications may be made without departing from the spirit and scope of the claims. For example, advantageous results still could be achieved if steps of the disclosed techniques were performed in a different order and/or if components in the disclosed systems were combined in a different manner and/or replaced or supplemented by other components. Accordingly, other implementations are within the scope of the following claims.

For example, the above-described methods, systems, and computer programs may be applied to all medical imaging services, even though some of the examples provided above are with respect to nuclear cardiology.

What is claimed is:

1. A computer implemented method for quantitatively assessing and managing the performance of a workflow process and an information flow process of a medical imaging service process, the method comprising:
    creating, by the computer, a model including activities related to the workflow process and information flow process of a medical imaging service, the workflow process and information flow process of the medical imaging service process being divided into a pre-testing phase, a testing phase, and a post-testing phase;
    wherein the pre-testing phase includes discrete steps that correspond validation activities from the workflow process with standardization activities from the information flow process, and test and indication activities from the workflow process with dissemination activities from the information flow process;
    wherein the testing phase includes discrete steps that correspond ordering activities from the workflow process with access activities from the information flow process, and reporting activities from the workflow process with distribution activities from the information flow process;
    wherein the post-testing phase includes discrete steps that correspond to follow-up activities from the workflow process with adoption activities from the information flow process;
    mapping, by the computer, the activities of the medical imaging service process model to the corresponding discrete steps of the workflow process and information flow process of the pre-testing phase, testing phase, and post-testing phase;
    receiving, by the computer, data generated for the activities performed during the discrete steps of each phase of the workflow process and information flow process by a plurality of patients participating in the medical imaging service process;
    receiving, by the computer, one or more known medical imaging service guidelines for comparison with the received patient-related data generated during performance of the activities related to the workflow process and information flow process of the medical imaging service;
    calculating, by the computer, statistically based workflow metrics for the entire imaging service process model using the received data generated during performance of the mapped activities, wherein the workflow metrics are calculated as a ratio of the total number of a particular occurrence per the total number of results in the sample or the time taken to arrive at a particular occurrence, the workflow metrics including validation activities, indication activities, ordering activities, reporting activities, and follow-up activities;

calculating, by the computer, statistically based information flow metrics for the entire imaging service process model using the received data generated during performance of the mapped activities, wherein the information flow metrics are calculated as a ratio of the total number of a particular occurrence per the total number of results in the sample or the time taken to arrive at a particular occurrence, the information flow metrics including, in terms of efficiency and accuracy, standardization activities, dissemination activities, access activities, distribution activities, and adoption activities;

determining, by the computer, outcome metrics for the plurality of patients using the received data generated in the performance of the mapped activities, the outcome metrics including one or more of diagnostic outcomes, clinical outcomes, service outcomes, and financial outcomes;

wherein the diagnostic outcome metrics summarize at least utilization, test accuracy, and clinical correlation related of the medical imaging service guideline;

wherein the clinical outcome metrics summarize at least event rates, symptoms, and testing indexes related to the medical imaging service guideline;

wherein the service outcome metrics summarize at least procedures, referrals, and satisfaction related to the medical imaging service guideline;

wherein the financial outcome metrics summarize at least reimbursed totals and averages, inadequate reimbursement, costs, and cost-benefits related to the medical imaging service guideline; and generating, by the computer, a user interface including a performance analysis of the activities in the mapped phases of the workflow process and information flow process based on one or more of the workflow metrics, information flow metrics, outcome metrics, and received data generated in the performance of the mapped activities.

2. The computer implemented method of claim 1 wherein calculating workflow metrics includes calculating, in the computer, the percentage of patients who have had risk assessment.

3. The computer implemented method of claim 2 wherein calculating workflow metrics includes calculating, in the computer, a ratio of a number of patients referred for testing to the number of patients indicated in the risk assessment as needing to be tested.

4. The computer implemented method of claim 3 wherein calculating information flow metrics includes calculating, in the computer, the amount of time elapsed before a predetermined percentage of patients have been referred.

5. The computer implemented method of claim 2 wherein calculating workflow metrics includes calculating, in the computer, a ratio of patients indicated in the risk assessment who are scheduled for testing to a total number of patients referred for testing.

6. The computer implemented method of claim 5 wherein calculating information flow metrics includes calculating, in the computer, the amount of time required to schedule indicated patients for testing.

7. The computer implemented method of claim 2 wherein calculating information flow metrics includes calculating, in the computer, the amount of time elapsed before a predetermined percentage of patients have had risk assessment.

8. The computer implemented method of claim 1 wherein calculating workflow metrics includes calculating, in the computer, a ratio of a number of patients selected for a given diagnostic test to a number of patients referred for testing by a referral physician.

9. The computer implemented method of claim 8 wherein calculating information flow metrics includes calculating, in the computer, a ratio of a number of patients correctly selected for a given diagnostic test to a total number of patients selected for a given diagnostic test.

10. The computer implemented method of claim 9 wherein calculating information flow includes calculating, in the computer, the amount of time taken to send test results to one of patients and referring providers.

11. The computer implemented method of claim 9 wherein calculating information flow includes calculating, in the computer, a ratio of a number of patients that have received test results to a total number of patients having test results.

12. The computer implemented method of claim 8 wherein calculating information flow metrics includes calculating, in the computer, the amount of time taken to select patients for testing from the time that the patients are referred for testing.

13. The computer implemented method of claim 1 wherein receiving data includes receiving data indicative of at least one of procedures, indications and reimbursement.

14. The computer implemented method of claim 13 wherein calculating workflow metrics and information flow metrics includes, in the computer, generating diagnostic metrics.

15. The method as in claim 13 wherein the diagnostic metrics include utilization metrics to track an impact of using a screening test in the medical imaging service process in at least one of further other non-invasive testing, invasive testing, interventional therapy, and surgery.

16. The computer implemented method of claim 13 wherein the diagnostics metrics include accuracy metrics representative of diagnostic test accuracy in terms of patients and specific anatomy in comparison to other invasive tests.

17. The computer implemented method of claim 13 wherein the diagnostics metrics include clinical correlation metrics to track feedback from referral physicians and patients themselves to results of tests.

18. The computer implemented method of claim 1 wherein calculating workflow metrics and information flow metrics includes, the computer, generating clinical outcome metrics.

19. The computer implemented method of claim 18 wherein the clinical outcome metrics include event rate metrics to track feedback related to clinical complications and events using a communications network.

20. The computer implemented method of claim 18 wherein the clinical outcome metrics include symptom metrics to track changes in a patient's symptoms.

21. The computer implemented method of claim 18 wherein the clinical outcome metrics include testing index metrics to measure physiological functions of a patient as a result of patient treatment.

22. The computer implemented method of claim 1 wherein calculating workflow metrics and information flow metrics includes, in the computer, generating service outcome metrics.

23. The computer implemented method of claim 22 wherein the service outcome metrics include procedure outcome metrics to track multiple procedure utilizations over a period of time at a particular medical imaging center as compared with at least one of benchmark targets and organizational goals.

24. The computer implemented method of claim 22 wherein the service outcome metrics include referral outcome metrics to track referral physician specialties, practice locations, referred patient's characteristics and referral potentials as compared with at least one of benchmark targets and organizational goals.

25. The computer implemented method of claim 1 wherein calculating workflow metrics and information flow metrics includes, in the computer, generating financial outcome metrics.

26. The computer implemented method of claim 25 wherein the financial outcome metrics include reimbursement metrics to measure a billing performance as a function of a reimbursement rate and speed compared to at least one of a benchmark target and organizational goals.

27. The computer implemented method of claim 1 wherein calculating workflow metrics includes calculating, in the computer, a ratio of a number of patients having test results delivered to a total number of patients having test results.

28. The computer implemented method of claim 1 further comprising generating analysis metrics based on an integration of different users of the communications network, different tests and results, and the process metrics to enable a comprehensive analysis of different aspects of the medical imaging services.

29. The computer implemented method of claim 28 wherein the analysis metrics include local practice analysis metrics and further comprising developing of local database system to measure and track the degree of standard implementation, the difference of patients and practice between national and local populations, and refinement of local standardization.

30. The method as in claim 29 wherein the local practice analysis metrics include metrics for use in measuring and tracking the degree of implementing national standards and guidelines for quality control, improve insurance reimbursement and monitoring legal protection.

31. The method as in claim 29 wherein the local practice analysis metrics include metrics to define the difference of patients and practice between national and local levels for patient population characteristics in disease development, progress and response to treatment as well as patient reception to new technologies and treatment.

32. The method as in claim 29 wherein the local practice analysis metrics include metrics to define the difference of practice between national and local level to identify local practice variation from national criteria and standards in diagnosis and diagnostic accuracies to redefine local standards in local practice or recommend new local practice criteria.

33. The computer implemented method of claim 28 the analysis metrics include referral analysis metrics and further comprising identifying referral patterns of referral physicians in relation to patients, tests, and process and outcome metrics.

34. The computer implemented method of claim 28 wherein the analysis metrics include clinical risk assessment metrics and further comprising performing at least one of pre-testing risk stratification and post-testing risk stratification using the clinical risk assessment metrics.

35. The computer implemented method of claim 28 wherein the analysis metrics include clinical risk assessment metrics to use an established or published model to assess risks in given patients and a need for further diagnostic imaging tests.

36. The computer implemented method of claim 28 wherein the analysis metrics include clinical risk assessment metrics to use an established or published model to assess risks in given patients and compare to post imaging risk classification to assess the established or published model.

37. The computer implemented method of claim 28 wherein the analysis metrics include behavior analysis metrics to evaluate behavior patterns of at least one of referral physicians, medical imaging centers, and patients compared to standards and outcomes in the model medical imaging process over a period of time.

38. The computer implemented method of claim 28 wherein the analysis metrics include organizational process analysis metrics further comprising identifying one or more steps in the entire process for improvement in organizational performance for different outcomes using the organizational process analysis metrics.

39. The method as in claim 1 further storing medical practice guidelines in a data store and comparing metrics from at least one of the discrete steps in the model medical imaging process to the medical practice guidelines in a computer.

40. The computer implemented method of claim 39 further comprising correlating the medical practice guidelines to modifiable reimbursement codes and recommendation levels.

41. The computer implemented method of claim 1 wherein receiving data includes receiving data from at least one of patients, medical personnel, medical imaging personnel, and organizations.

42. The computer implemented method of claim 1 further comprising identifying one or more limiting steps in the model medical imaging service process using at least one of the information flow metrics and the workflow metrics.

43. The computer implemented method of claim 1 wherein receiving data includes receiving, in the computer, data indicative of procedures, indications, and reimbursement.

44. The computer implemented method of claim 1 further comprising presenting at least one of the information flow metrics and the workflow metrics to a user in an order following the discrete steps in the model medical imaging service process to enable the user to identify one or more limiting steps.

* * * * *